US012186526B2

(12) United States Patent
Nakamura

(10) Patent No.: US 12,186,526 B2
(45) Date of Patent: Jan. 7, 2025

(54) DRUG SOLUTION ADMINISTRATION UNIT, DRUG SOLUTION ADMINISTRATION MODULE, DRUG SOLUTION ADMINISTRATION DEVICE, AND MEDICATION MANAGEMENT SYSTEM

(71) Applicant: atDose Co., Ltd., Kanagawa (JP)

(72) Inventor: Hidenori Nakamura, Yokohama (JP)

(73) Assignee: atDose Co., Ltd., Yokohama (JP)

(*) Notice: Subject to any disclaimer, the term of this patent is extended or adjusted under 35 U.S.C. 154(b) by 568 days.

(21) Appl. No.: 17/608,912

(22) PCT Filed: Jul. 28, 2020

(86) PCT No.: PCT/JP2020/028950
§ 371 (c)(1),
(2) Date: Nov. 4, 2021

(87) PCT Pub. No.: WO2021/199454
PCT Pub. Date: Oct. 7, 2021

(65) Prior Publication Data
US 2022/0313907 A1    Oct. 6, 2022

(30) Foreign Application Priority Data

Apr. 1, 2020 (JP) ................................ 2020-065560

(51) Int. Cl.
*A61M 5/14* (2006.01)
*A61M 5/168* (2006.01)
(52) U.S. Cl.
CPC ...... *A61M 5/1409* (2013.01); *A61M 5/16877* (2013.01); *A61M 2205/3303* (2013.01)

(58) Field of Classification Search
CPC ............ A61M 5/16877; A61M 5/1409; A61M 2205/3303; A61M 31/002;
(Continued)

(56) References Cited

U.S. PATENT DOCUMENTS 10,149,938 B2 * 12/2018 Murphy ................. G16H 40/67
10,359,038 B2 *  7/2019 van Boeyen .......... F04B 45/053
(Continued)

FOREIGN PATENT DOCUMENTS

EP    0361688 A1 *  4/1990
EP    0543259 A1     5/1993
(Continued)

OTHER PUBLICATIONS

Japanese Office Action issued on Apr. 22, 2020 of corresponding application No. 2020-065560; 6 pages.
(Continued)

*Primary Examiner* — Kami A Bosworth
(74) *Attorney, Agent, or Firm* — Maier & Maier, PLLC

(57) ABSTRACT

A drug solution administration unit including a drug solution administration module having a first flow path unit, a second flow path unit, and a drive mechanism unit, and a drug solution administration device having a branch path and a main path. The first flow path unit includes an upstream side main body where a first flow path to store drive solution is formed, and the second flow path unit includes a downstream side main body where a second flow path to store drug solution is formed. The drive mechanism unit includes a pair of electrodes and a porous body sandwiched between the pair of electrodes, the drive mechanism unit has a connecting flow path connecting a downstream end of the first flow path and an upstream end of the second flow path.

5 Claims, 17 Drawing Sheets

(58) Field of Classification Search
CPC .... A61M 2005/14513; A61M 5/16804; A61M 5/1407; A61M 5/16827; B01L 2400/0415; B01L 3/50273; B01L 3/502715; B01L 2400/0418; B01L 2300/0645; A61N 1/30; A61N 1/0448; A61N 1/325; A61N 1/0436; F04B 19/006

See application file for complete search history.

(56) References Cited

U.S. PATENT DOCUMENTS

| | | | |
|---|---|---|---|
| 2010/0191223 A1* | 7/2010 | Togawa | A61M 5/14244 604/67 |
| 2014/0088506 A1* | 3/2014 | Heller | F04D 13/06 264/618 |
| 2021/0100948 A1 | 4/2021 | Hirafuji | |

FOREIGN PATENT DOCUMENTS

| | | |
|---|---|---|
| JP | H05-317421 A | 12/1993 |
| JP | 2008-504794 A | 2/2008 |
| WO | WO 86/03418 A1 * | 6/1986 |
| WO | 2009/048144 A1 | 4/2009 |
| WO | 2015/059766 A1 | 4/2015 |
| WO | 2018/194041 A1 | 10/2018 |

OTHER PUBLICATIONS

International Search Report issued on Jun. 10, 2020 in corresponding International application No. PCT/JP2020/028950; 5 pages.
Extended European Search Report issued on Jan. 9, 2023, in corresponding European Application No. 20 92 9501.3, 8 pages.
India Examination Report issued on Mar. 27, 2023, in corresponding India Application No. 202017054642; 6 pages.

* cited by examiner

DRUG SOLUTION ADMINISTRATION UNIT, DRUG SOLUTION ADMINISTRATION MODULE, DRUG SOLUTION ADMINISTRATION DEVICE, AND MEDICATION MANAGEMENT SYSTEM

FIELD

This invention relates to a drug solution administration unit, a drug solution administration module, a drug solution administration device, and a medication management system that adjust the dose of a drug solution.

BACKGROUND

In a medical field, an intravenous injection is performed to administer a drug solution or the like gradually by placing an injection needle in a vein. In intravenous injections, such method has been adopted as letting drug solution flow through a syringe pump via a three-way stopcock to be mixed with infusion that flows from an infusion container through a tube for intravenous injection. The syringe pump can arbitrarily set the flow rate of the drug solution (see, for example, Patent Literatures 1 and 2).

CITATION LIST

Patent Literature

Patent Literature 1: JP, 201.7-213057, A
Patent Literature 2: J 2004-173844, A

SUMMARY

However, the current general syringe pump cannot be placed right next to the patient due to the big size of the pump itself, and the pump should be placed at a position one meter or more away from the patient; and in this condition the pump should be operated. As the distance from the patient increases, the distance from the pump to the intravenous tube becomes longer, so it takes time and efforts to remove air bubbles in the tube and, at the same time, and it is difficult to stabilize the internal pressure of the tube.

This present invention has been made to solve the above-mentioned problems and aims to offer drug solution administration unit, drug solution administration module, drug solution administration device and medication management system that realize quick and stable administration of drug solution without hassles.

A drug solution administration unit which is related to one aspect of this invention includes a drug solution administration module having a first flow path unit including an upstream main body where a first flow path to store drive solution is formed, a second flow path unit including a downstream main body where a second flow path to store a drug solution is formed, and a drive mechanism unit including a pair of electrodes and a porous body sandwiched between the pair of electrodes, and a connecting flow path connecting a downstream end of the first flow path and an upstream end of the second flow path is formed; and a drug solution administration device having a housing where a containment unit is formed to store the drug solution administration module, and inside of the housing, having a branch path where the second flow path is connected and a main path that is branched from a downstream side of the branch path and connected to an intravenous tube wherein the drug solution administration module has a drug solution connecting unit at a downstream end of the second flow path, and wherein the drug solution administration device has a flow path connecting unit at an upstream end of the branch path to which the drug solution connecting unit is connected.

A drug solution administration module which is related to one aspect of the present invention, is mounted at a drug solution administration device, having a first flow path unit including an upstream side main body where a first flow path to store drive solution is formed, a second flow path unit that includes a downstream side main body where a second flow path to store drug solution is formed, and a drive mechanism unit including a pair of electrodes and a porous body sandwiched between the pair of the electrodes, where a connecting flow path is formed to connect a downstream end of the first flow path and an upstream end of the second flow path, and having a drug solution connecting unit at a downstream end of the second flow path, having a housing where a containment unit is formed, and, inside of the housing, having a branch path where a flow path connecting unit is provided at an upstream end and a main path that is separated from the downstream side of the branch path and connected to an intravenous tube, while the drug solution connecting unit is being connected to the flow path connecting unit, stored in the containment unit.

The drug solution administration device related to an aspect of the present invention has a housing in which a containment unit is formed. The drug solution administration device has, inside the housing, a branch path where a flow path connecting unit is formed at an upstream end and a main path branched from the downstream side of the branch path and connected to an intravenous tube. The drive solution administration module has a first flow path unit including an upstream side main body where a first flow path to store drive solution is formed; a second flow path unit including a downstream side main body and a second flow path where a drug solution connecting unit is provided at a downstream end to store drug solution is formed; and a drive mechanism unit including a pair of electrodes and a porous body sandwiched between the pair of electrodes; and the drive mechanism unit having a flow path connecting unit connecting a downstream end of the first flow path and an upstream end of the second flow path. The drug solution administration module, being contained in the containment unit in a state in which the drug solution connecting unit is connected to the flow path connecting unit, is mounted to a drug solution administration device comprising a control unit being connected to the pair of electrodes for controlling an operation of the drive mechanism unit.

A drug solution administration unit which is related to one aspect of the present invention, has a plurality of the drug solution administration device described above, and while associating with each other, respective control units of the plurality of drug solution administration devices control the operation of the drive mechanism unit of the drug solution administration module that is associated to itself.

A medication management system which is related to one aspect of the present invention includes the above-mentioned drug solution administrative device, an analysis processing device to analyze a personal data that includes attribute information of a patient and a drug solution data that includes flow rate information of a drug solution of a drug solution administration module, and a management device having a display unit, and the display unit displays information based on the result of analysis by the analysis processing device.

According to the present invention, a connecting flow path that connects the downstream end of the first flow path and the upstream end of the second flow path is configured to the porous body and a pair of electrodes that sandwiches the porous body, while the second flow path being connected to the branch path of the drug solution administration device and the downstream side of the branch path is connected to the main path connected to the intravenous tube. Therefore, due to the electric penetration flow because of the potential difference between a pair of electrodes, the drive solution permeated into the porous body flows towards the downstream side through the connecting flow path, corresponding to the application of voltage to the pair of electrodes. The drug solution within the second flow path is immediately pushed out towards the downstream side, quick and stable administration of the drug solution can be realized without hassles.

DETAILED DESCRIPTION

First Embodiment

Figure 1:
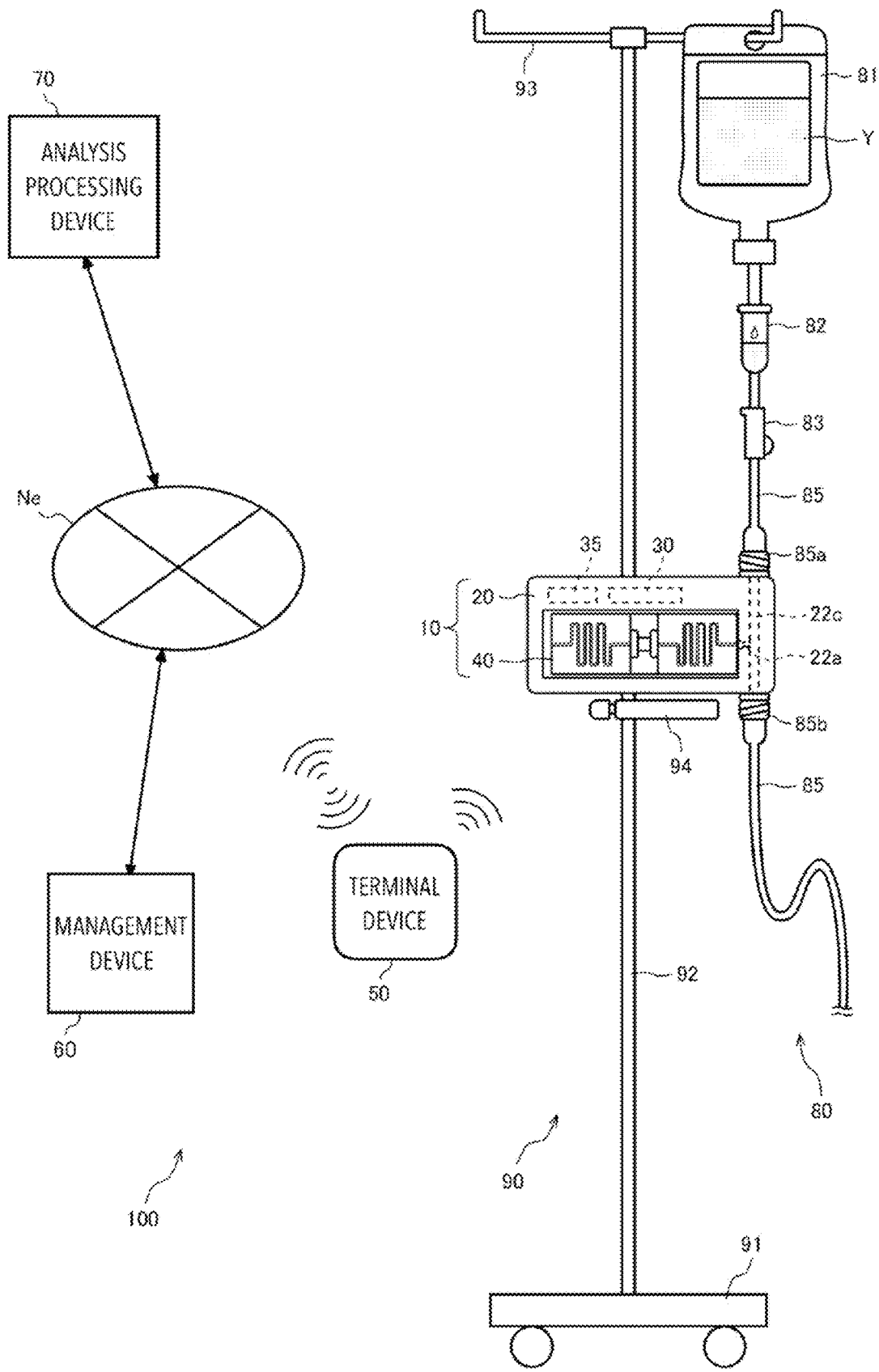
FIG. 1 is a diagram illustrating a medication management system and its peripheral equipment or the like according to Embodiment 1 of the present invention.

With reference to FIG. 1, a medication management system and its peripheral devices according to the first embodiment will be described. Further, in each of the following drawings, a part of the reference numerals may be omitted to avoid complication. As shown in FIG. 1, the medication management system 100 includes a drug solution administration unit 10, a terminal device 50, a management device 60, and an analysis processing device 70. The terminal device 50, the management device 60, and the analysis processing device 70 are communicably connected via a network Ne such as the internet or the like.

The drug solution administration unit 10 includes a drug solution administration device 20 and a drug solution administration module 40, and is used in combination with the intravenous unit 80 in the medical field. The drug solution administration module 40 is configured to be attachable to and detachable from the drug solution administration device 20. The intravenous unit 80 has, for example, an infusion container 81 in which the infusion Y is stored, an intravenous tube 82, a klemme 83, and an injection needle (not shown). The infusion container 81, the intravenous tube 82, the klemme 83, and the injection needle are connected by a tube 85.

Here, the stand 90 illustrated in FIG. 1 is attached to the leg portion 91 with the casters, a column 92 extending upward from the leg portion 91, a bottle hook 93 connected to the upper end of the column 92, and a handle portion 94 attached to the column 92. For example, the intravenous unit 80 is used with the infusion container 81 is hooked on the bottle hook 93. The tube 85 is separated by the upstream side connector 85a and the downstream side connector 85b. The injection needle is kept in the vein of a person during infusion. The drug solution administration unit 10 is fixed to either the column 92 or the handle portion 94 or the like via a fixing member (not shown). However, the drug solution administration unit 10 may be placed on a table or the like.

The terminal device 50 is a remote controller for setting and operating the drug solution administration unit 10, or a mobile terminal such as a smart phone or a tablet terminal or the like. When the terminal device 50 is a mobile terminal, it is assumed that an application program for setting and operating the drug solution administration unit 10 has been downloaded and installed in advance.

The management device 60 is a PC (Personal Computer) provided in a facility such as a hospital and used by a medical staff or the like. The PC includes a Tablet PC, a Notebook PC, a Desktop PC, and the like. Although FIG. 1 illustrates one drug solution administration unit 10 and one management device 60 as the configuration of the medication management system 100, the medication management system 100 may include a plurality of drug solution administration units 10. Alternatively, a plurality of management devices 60 may be included. This is because it is assumed that a plurality of drug solution administration units 10 are used in an actual medical field, and the analysis processing device 70 collects, accumulates, and analyzes various data obtained from a plurality of management devices 60. That is, the management device 60 has a function of managing the setting data corresponding to each of the plurality of drug solution administration units 10. The setting data includes personal data including information on the attribute of the patient, and drug solution data including information on the flow rate of the drug solution C. In addition, a plurality of management devices 60 may be installed in one medical site.

The analysis processing device 70 is configured by a cloud server based on cloud computing, a physical server, a system combining these, or the like. The analysis processing device 70 collects the setting data of the drug solution administration unit 10 managed by each management device 60 from the management devices 60 placed in medical sites around the world. The analysis processing device 70 may collect the setting data from the terminal device 50. The analysis processing device 70 accumulates the collected setting data and analyzes the accumulated setting data.

The drug solution administration unit 10 may be configured to communicate with the terminal device 50, the management device 60, or the analysis processing device 70, via network Ne. However, a network failure in a medical institution is feared to lead to halt hospital functions, hence, security measures against hacking or the like is also important. Therefore, the drug solution administration unit 10 according to the first embodiment is from the view point of safety, credibility and the like only capable of communication using a so-called in-hospital LAN (Local Area Network) or the like, and the network is provided via the terminal device 50. It is designed to communicate with devices on Ne.

Figure 2:
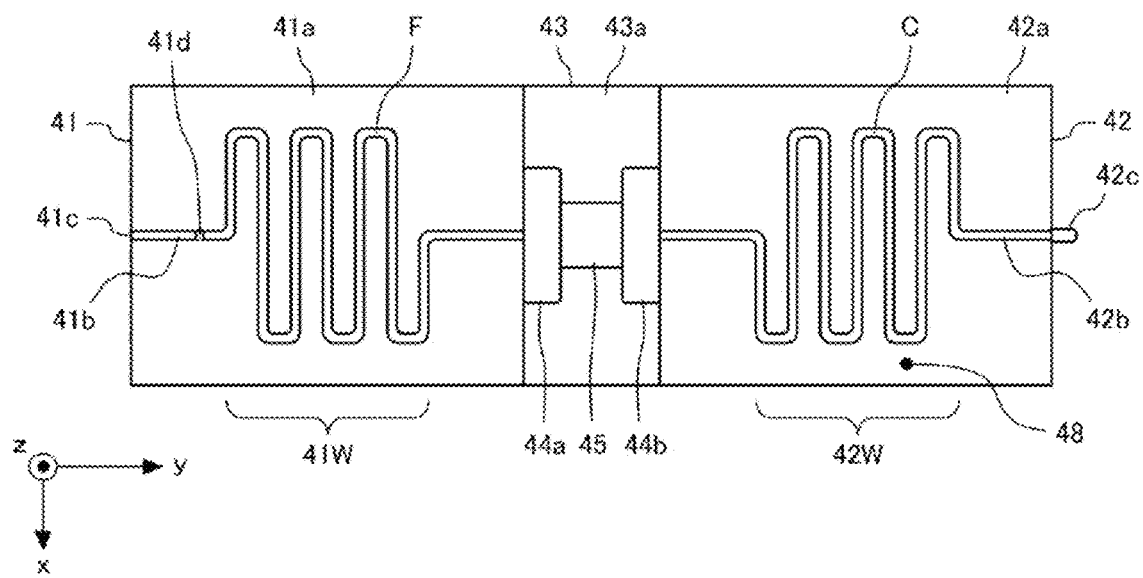
FIG. 2 is a diagram illustrating the external appearance of the drug solution administration module of FIG. 1.
Figure 3:
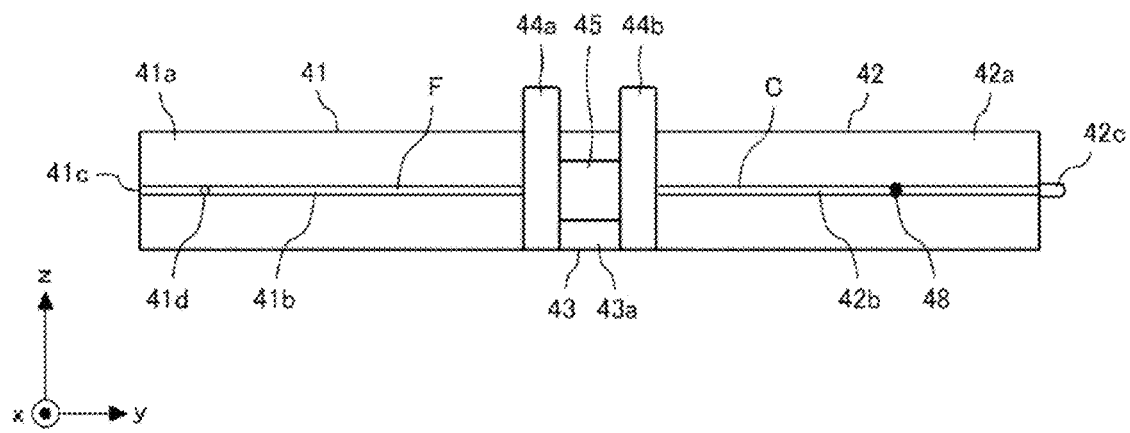
FIG. 3 is a diagram when the drug solution administration module of FIG. 2 is seen from the side.

Next, the specific configuration of the drug solution administration module 40 will be described with reference to FIG. 2 and FIG. 3. Hereinafter the drug solution administration module 40 is also referred to as "module 40". In FIG. 2 and FIG. 3, in order to indicate the orientation of the module 40, the x-axis, the y-axis, and the z-axis are shown. Regarding the module 40, the x-axis direction is the bending direction, the y-axis is the administration direction, and the z-axis is the thickness direction. The same applies to the following figures.

As shown in FIG. 2 and FIG. 3, the module 40 has a first flow path unit 41, a second flow path unit 42, a drive mechanism unit 43. The first flow path unit 41 contains the upstream side main body 41a in which the first flow path 41b that stores the drive solution F is formed. The drive solution F may be a liquid that can be used for electroosmotic flow pump such as water and alcohols. The second flow path unit 42 includes a downstream side main body 42a having a second flow path 42b in which the drug solution C is stored. In FIG. 2, the meandering shape that meanders in the bending direction is illustrated as the shape of the bending portion 41W and the bending portion 42W. By not only the first flow path 41b but also the second flow path 42b are in a curved shape, the remaining amount of the drug solution C can be easily confirmed from the second flow path 42b. Regarding the flow path in the module 40, the first flow path 41b is located upstream of the drive mechanism unit 43, and the second flow path unit 42 is located downstream of the drive mechanism unit 43.

The upstream side main body 41a is formed of resin, and the first flow path 41b is formed by cutting, for example. The drive solution F flows towards the downstream side of the first flow path 41b by the action of the drive mechanism unit 43. The first flow path 41b has a bending portion 41W for securing the liquid volume and suppressing convection. At the downstream end of the first flow path 41b, a vent hole 41c having a size that prevents liquid leakage is provided. In the first flow path 41b of the first embodiment of the present implementation, a following member 41d that follows at the end of the drive solution F is arranged. By visually observing the following member 41d, the approximate remaining amount of the drug solution C can be confirmed.

The downstream side main body 42a is formed by resin, and the second flow path 42b is formed by cutting, for example. Due to the action of the drive mechanism unit 43, the second flow path 42b allows the drug solution C to flow downstream. The second flow path 42b has a bending portion 42W for securing a liquid amount and suppressing convection. The upstream end of the second flow path 42b is provided with a drug solution connecting unit 42c connected to a flow path connecting unit 22b of the drug solution administration device 20 described later. In the module 40 according to the first embodiment of the present invention, the downstream side main body 42a is provided with a remaining amount sensor 48 including, for example, an optical sensor. The remaining amount sensor 48 transmits remaining amount information regarding the remaining amount of the drug solution C to the communication processing unit 30 as needed or periodically. The remaining amount sensor 48 may transmit remaining amount information in response to a request from the communication processing unit 30.

The drive mechanism unit 43 has a drive unit main body 43a that is made of resin. The drive mechanism unit 43 includes an electrode 44a and an electrode 44b, which are a pair of electrodes, and a porous body 45 sandwiched between the electrode 44a and the electrode 44b. The electrodes 44a and 44b are formed of, for example, a conductive substance and rubber, and have conductivity. Each of the electrodes 44a and 44b is provided with a terminal (not shown) connected to the communication processing unit 30 described later. The terminal of the upstream electrode 44a is a positive terminal, and the terminal of the downstream electrode 44b is a negative terminal. The porous body 45 is connected to the first flow path 41b via the electrode 44a, and the drive solution F has permeated therein. The porous body 45 is formed of, for example, a porous ceramic.

Hereby, when a voltage is applied to both ends of the porous body infiltrated with the liquid, a phenomenon where the liquid in the porous body moves from the one electrode side to the other electrode side. This phenomenon is called an electroosmotic flow phenomenon, and the liquid flow generated by the phenomenon is called as electroosmotic flow. In the drive mechanism unit 43, the drive solution F has infiltrated into the porous body 45, and a pair of the electrodes (44a, 44b) are arranged at the positions facing each other across the porous body 45. Therefore, the drive mechanism unit 43 functions as an electroosmotic flow pump by applying a voltage to the pair of the electrodes (44a, 44b).

The drive mechanism unit 43 is formed with a connecting flow path that connects the downstream end of the first flow path 41b and the upstream end of the second flow path 42b. The connecting flow path is an opening that passes through between the electrode 44a and the porous body 45 and the electrode 44b. At least a part of the pair of the electrodes (44a, 44b) and the porous body 45 is covered by the drive unit main body 43a.

The drive mechanism unit 43 stops its drive when the drive solution F in the first flow path 41b is exhausted. That is, in the module 40, the drive mechanism unit 43 automatically stops when the drive solution F within the first flow path 41b has completely flowed to the downstream side, and even if a voltage is applied to the pair of electrodes (44a, 44b), the flow does not occur in the flow path. Here, the first flow path 41b and the connecting flow path are filled with the drive solution F, and the second flow path 42b is filled with the drug solution C. The drive solution F infiltrates the porous body 45. Therefore, by adjusting the entire module 40 so as to maintain the drive solution F slightly less than the drug solution C, the drive mechanism unit 43 functions as a safety mechanism for preventing the drive solution F from mixing with the infusion Y. Considering manufacturing errors and the like, the amount of the drive solution F may be adjusted to be about 95% of the amount of the drug solution C. In other words, the amount of the drug solution C is preferably about 105% to 110% of the amount of the drive solution F. The amount obtained by subtracting the amount of the drive solution F from the amount of the drug solution C when adjusted in this way is called an 'adjustment amount'.

Next, with reference to FIG. 4, the configuration of the drug solution administration device 20 and the positional relationship and connection relationship between the drug solution administration device 20 and the module 40 will be described. The drug solution administration device 20 includes a branch path 22a to which the downstream end of the second flow path 42b is connected, and a main path 22c branched from the downstream side of the branch path 22a and connected to the tube 85 for infusion. More specifically, the branch path 22a is provided with a flow path connecting unit 22b at the upstream end, and the drug solution connecting unit 42c of the second flow path unit 42 is connected to the flow path connecting unit 22b.

The drug solution administration device 20 has a housing 21 that forms an outer shell; inside the housing includes an output unit 35 that outputs information and the like regarding the remaining amount of the drug solution C and a communication processing unit 30 in which appropriately adjusted voltage is applied to a pair of the electrodes (44a, 44b). The housing 21 has a main path 22c, and a tube 85 on the upstream side thereof, that is, an upstream connecting unit 21a for connecting the main path 22c and the upstream side connector 85a. The housing 21 has a main path 22c and a tube 85 on the downstream side thereof, that is, a downstream connecting unit 21b for connecting the main path 22c and the downstream side connector 85b.

Further, in the housing 21, the containment unit 21c is formed to enclose the module 40. In FIG. 4, the groove shaped containment unit 21c is illustrated. The communication processing unit 30 has a power supply terminal (not shown), either directly or through a conductor or the like, connected to each of the terminals of the pair of electrodes (44a, 44b). That is, the module 40 is contained in the containment unit 21c of the housing 21, the drug solution connecting unit 42c is connected to the flow path connecting unit 22b, and each power supply terminal is connected to each of the terminals of the pair of electrodes (44a, 44b) and thus mounted to the drug solution administration device 20. Thereby, the medication management system 100 can pass the infusion Y flowing from the infusion container 81 through the tube 85 to the main path 22c, and mix the drug solution C from the branch path 22a into the infusion Y passing through the main path 22c.

Figure 5:
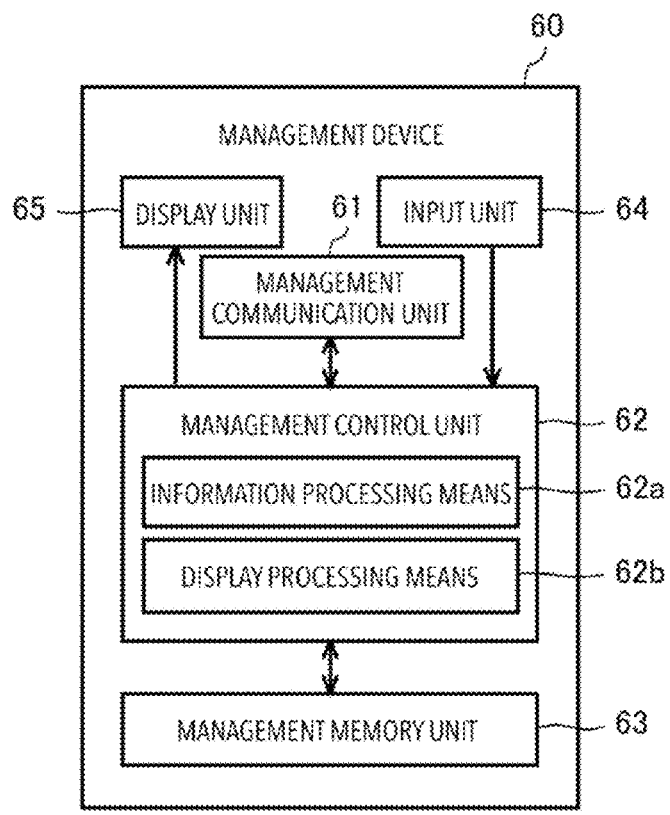
FIG. 5 is a block diagram illustrating the functional configuration of the management device of FIG. 1.

Next, with reference to FIG. 5, the functional configuration of the management device 60 will be described. The management device 60 includes a management communication unit 61, a management control unit 62, a management memory unit 63, an input unit 64, and a display unit 65. The management communication unit 61 is an interface for the management device 60 to perform wired or wireless communication with external devices such as the drug solution administration device 20, the terminal device 50, and the analysis processing device 70 and the like. In the management memory unit 63 stores various information and the like in addition to the operation program of the management control unit 62. The management memory unit 63 can be configured with a RAM (Random Access Memory) and a ROM (Read Only Memory), a PROM (Programmable ROM) such as a flash memory or an HDD (Hard Disk Drive) and the like.

The input unit 64 includes, for example, a keyboard and a pointing device such as a mouse, a track ball or the like. The input unit 64 receives an input operation by the user and transmits an operation signal according to the content of the input operation to the management control unit 62. The display unit 65 includes, for example, an LCD (Liquid Crystal Display), and displays various information according to an instruction from the management control unit 62.

The management control unit 62 has an information processing means 62a and a display processing means 62b. The information processing means 62a executes processing in response to information input from external devices via the management communication unit 61 and operation signals sent from the input unit 64. For example, when the information processing means 62a receives an operation related to display on the display unit 65, the information processing means 62a outputs a control signal according to the operation to the display processing means 62b.

The information processing means 62a receives, via the input unit 64, the input and configuration of the attribute data to show the attributes of the patient, medical history data to show the medical history of a patient, vital data of the patient, external data indicating the surrounding environment of the patient, and the kinship data related to the relatives including the family of the patient and the like. And the information processing means 62a makes these data as individual data and causes the management memory unit to store such data. The attribute data includes the information such as the patient's age, sex, weight, height, race, place of birth, nationality, and blood type. The medical history data includes information such as the patient's medical history, medication history, surgical record, and the like. The vital data includes the information such as a patient's heart rate, body temperature, blood pressure, blood glucose level, blood hormone level, respiration, body weight, urine volume, electroencephalogram and the like. The external data includes information such as temperature, humidity, atmospheric pressure, and the degree of noise around the patient, and the like. The kinship data includes at least one of attribute data of the relatives of a patient, medical history data, vital data, and external world data. The individual data can include at least one of the above information.

Among the attribute data, those useful for analysis and prediction include age, sex, and weight. Among the vital data, blood pressure, urine volume, and the like are useful for analysis and prediction. And when a certain drug solution C is administered, the external data such as season, attribute data such as sex and race, the career data such as medical history and medication history and will also influence upon the change of the vital data: therefore, such data can also be important factors for analysis and prediction.

The information processing means 62a receives the input via the input unit 64 and the composition of the drug solution data concerning the composition of the drug solution C and lets the management memory unit 63 memorize it. The drug solution data is associated with module information which is identification information individually set in the module 40. The drug solution data includes, in addition to the type of the drug solution C and the flow rate of the drug solution C, at least one information out of the dose of the drug solution C at one time, the timing of the administration of the drug solution C, the continuous administration time of the drug solution C, the repeated times of the administration of the drug solution C by the module 40. The dose of the drug solution C is the amount of the drug solution C that is continuously administered at one time, and the flow rate of the drug solution C is the rate at which the drug solution C is administered by the module 40. Out of the drug solution data, information indicating the flow rate of the drug solution C is referred as the flow rate data, and information indicating the timing of administration of the drug solution C is referred to as administration data. Hereinafter, the flow rate of the drug solution C is also simply referred to as "flow rate". The information processing means 62a transmits the setting data in which the personal data is associated with the drug solution data to the terminal device 50.

The display processing means 62b causes the display unit 65 to display characters, images and the like on the display screen or to switch the display of part or all of the display screen, according to the control signal output from the information processing means 62a. For example, the display processing means 62b causes the display unit 65 to display the medication control screen based on information such as prediction data and the like transmitted from the analysis processing device 70. That is, the display processing means 62b has a function of visually displaying all the data dealt by the medication management system 100, such as personal data of a plurality of patients, and analysis data, prediction data and the like obtained by machine learning on the display unit 65.

The management control unit 62 can be configured by an arithmetic device such as a CPU (Central Processing Unit), a GPU (Graphics Processing Unit) or the like and the operation program that co-operates with the arithmetic device to realize the above-mentioned various functions. It should be noted that, instead of the input unit 64 and the display unit 65, the management device 60 preferably has a touch panel including a display panel to display characters or the images and a detection means to detect those touch operations stacked on this concerned display panel. That said, however, the management device 60 may have both a touch panel and a mouse, a keyboard and the like.

Figure 6:
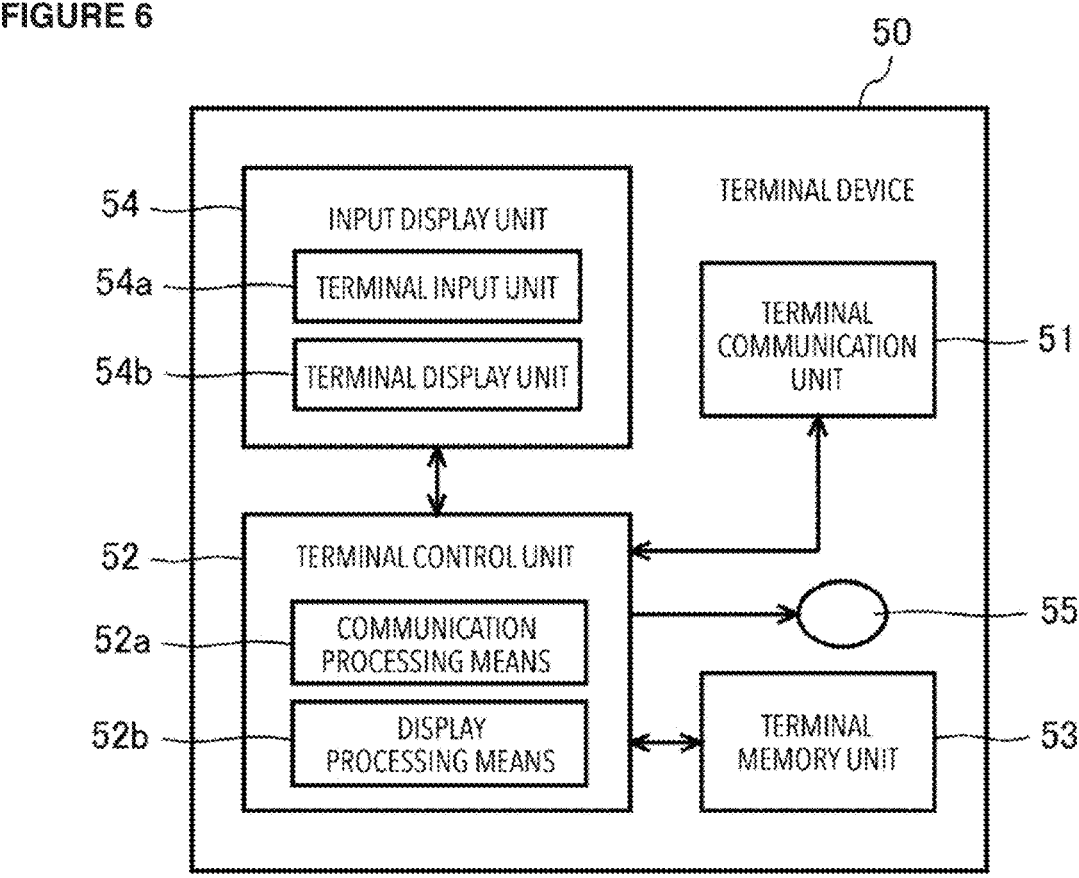
FIG. 6 is a block diagram illustrating the functional configuration of the terminal device of the FIG. 1.
Figure 7:
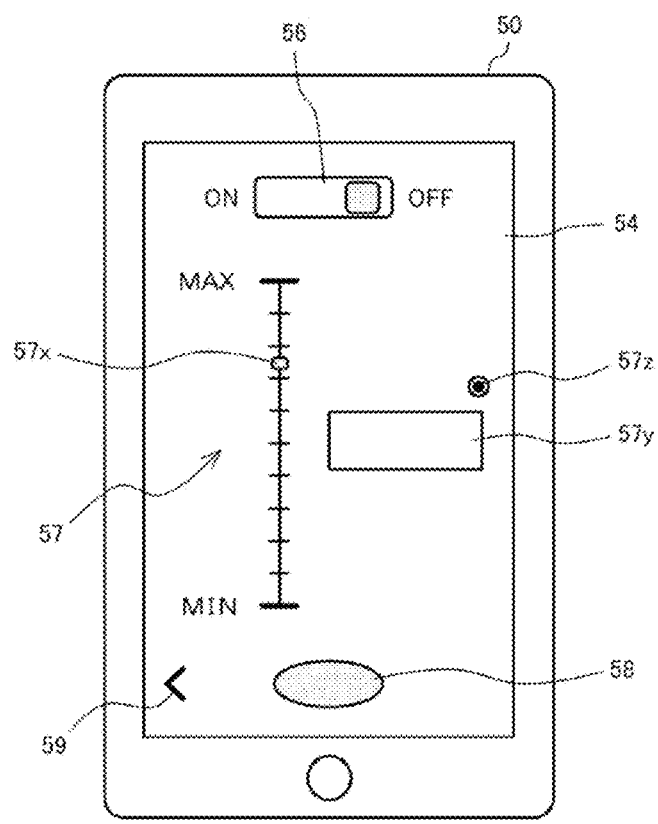
FIG. 7 is an explanatory drawing illustrating the confirmation operation screen displayed on the display unit of a terminal device of FIG. 6.

Next, the functional configuration of the terminal device 50 will be described with reference to FIG. 6 and FIG. 7. The terminal device 50 includes a terminal communication unit 51, a terminal control unit 52, a terminal memory unit 53, an input display unit 54, and a notification unit 55. The terminal communication unit 51 is an interface for the terminal device 50 to communicate with a device connected to the network Ne and a device connected wirelessly. In addition to the wireless standard in LPWA (Low Power Wide Area), the terminal communication unit 51 is based on wireless communication standards such as Bluetooth (registered trademark, the same applies hereinafter), BLE (Bluetooth Low Energy), WiFi (registered trademark, the same applies hereinafter) and the like. The terminal memory unit 53 stores various information in addition to the operation program of the terminal control unit 52. Terminal memory unit 53 is configured by a flash memory, an eMMC (embedded Multi Media Card), an SSD (Solid State Drive) or the like.

The input display unit 54 is a touch panel configured by laminating a terminal input unit 54a and a terminal display unit 54b. The terminal input unit 54a receives an input operation by the user and outputs a signal according to the content of the input operation to the terminal control unit 52. More specifically, the terminal input unit 54a detects a position or the like touched by the user and outputs information on the detected position and the like to the terminal control unit 52. The terminal display unit 54b is composed of, for example, a liquid crystal display, and displays characters or images. The notification unit 55 is configured including a speaker and notifies sound or voice.

The terminal control unit 52 has the communication processing means 52a and a display processing means 52b. When the communication processing means 52a acquires the setting data for each patient via the terminal communication unit 51, the communication processing means 52a makes the terminal memory unit 53 to store the acquired setting data. Further, when the communication processing means 52a receives an operation related to display on the terminal display unit 54b, it outputs a control signal corresponding to the concerned operation to the display processing means 52b. The display processing means 52b causes the terminal display unit 54b to display characters, images, and the like according to the control signal from the communication processing means 52a.

Here, with reference to FIG. 7, the confirmation operation screen displayed on the terminal display unit 54b will be described. The confirmation operation screen is a screen for confirming the state of the drug solution administration unit 10 and adjusting the flow rate. The display processing means 52b causes, in response to the operation by the user, the input screen of the device information displayed that is the identification information individually set in the drug solution administration device 20. The display processing means 52b causes the terminal display unit 54b to display the confirmation operation screen, as shown in FIG. 7, if the device information is input at the said input screen and the display of the confirmation operation screen is instructed. The confirmation operation screen according to the first embodiment of the present invention includes a safety switch 56, a slide bar 57 having a vertically movable cursor 57x, a flow rate display unit 57y, a status display unit 57z, an instruction button 58, and a return button 59.

The safety switch 56 is for preventing an unplanned change in setting due to a mistaken touch, and when it is in the ON state, the cursor 57x of the slide bar 57 cannot be moved. The cursor 56x indicates the current flow rate of the drug solution C and the corresponding flow rate value is displayed on the flow rate display unit 57y. The status display unit 57z, indicates whether the module 40 is administering the drug solution C. The display processing means 52b may preferably turn on the safety switch 56 when the confirmation operation screen is displayed. When the safety switch 56 is in the OFF state, the display processing means 52b receives the user's operation of the cursor 57x up and down, and changes the value of the flow rate display unit 57y in conjunction with the movement of the cursor 57x. When the user presses the instruction button 58, the communication processing means 52a transmits the flow rate data indicating the flow rate of the drug solution C set on the confirmation operation screen to the communication processing unit 30. The communication processing unit 30 adjusts the voltage applied to the pair of electrodes (44a, 44b) and updates the flow rate of the drug solution C according to the flow rate data.

The terminal control unit 52 can be configured by an arithmetic device such as a CPU, a GPU or the like and an operation program that co-operates with the arithmetic device to realize the above-described various functions. FIG. 6 shows an example in which the input display unit 54 is a touch panel, but the input display unit 54 is not limited to this. The terminal input unit 54a may be a pointing device such as a mouse, a keyboard, or the like, and the terminal input unit 54a and the terminal display unit 54b may be separated from each other.

Figure 8:
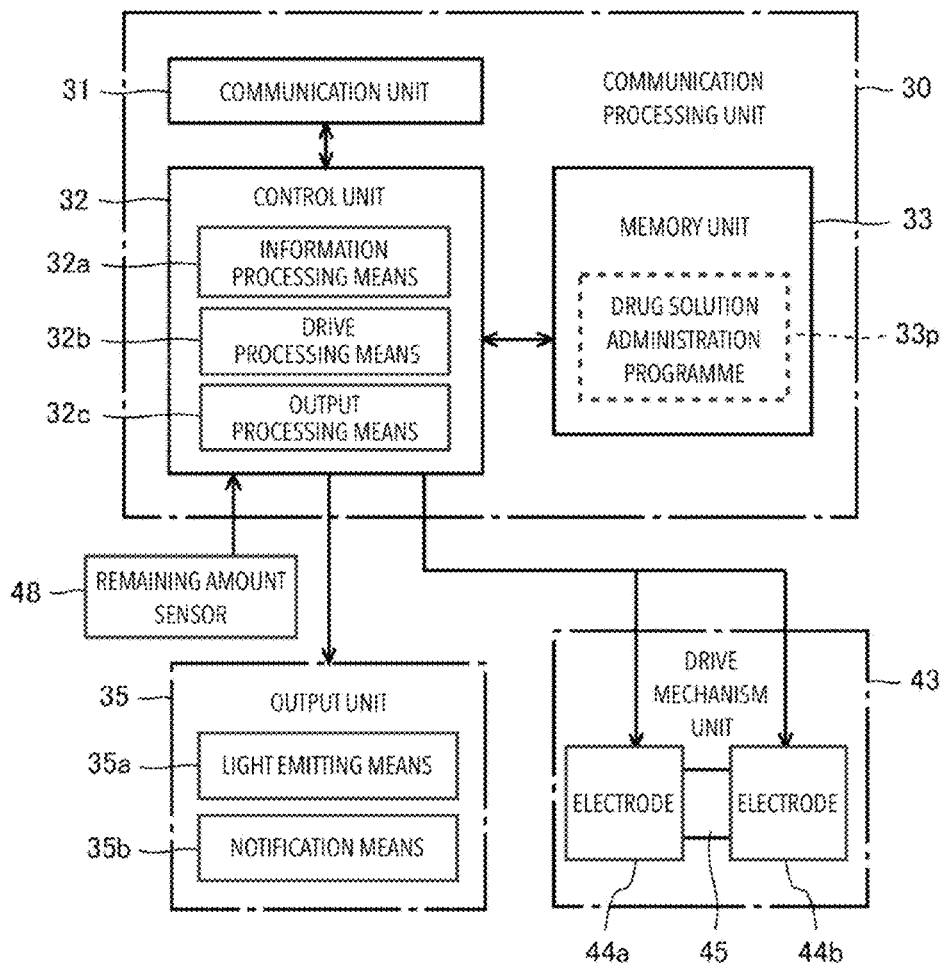
FIG. 8 is a bloc diagram illustrating a functional configuration of a communication processing unit and its relevant device in FIG. 2.

Next, in reference to FIG. 8, the functional configuration of the communication processing unit 30 of the drug solution administration device 20 and its related devices will be described. The communication processing unit 30 operates by power supply from a commercial power supply, a rechargeable power supply, or a battery such as a button battery. If the communication processing unit 30 has a specification of using a commercial power source, it will have a plug for inserting into an outlet, and may have a secondary battery or the like in case of a power failure or the like. The communication processing unit 30 can be portable if it has a specification that uses a rechargeable power source or a battery. Therefore, it is possible to improve usability and contribute to home medical care and facilitation of medication in the event of a disaster.

The communication processing unit 30 has the communication unit 31, a control unit 32, and a memory unit 33. The communication unit 31 is an interface for the communication processing unit 30 to communicate with the terminal device 50 and the like. The communication unit 31 has a function of performing data communication via the configuration of wireless communication standards such as Bluetooth, BLE, WiFi and the like, in addition to a wireless standard of LPWA.

The memory unit 33 memorizes various data in addition to the operation programs of the control unit 32 such as the drug solution administration program 33p. For example, the memory unit 33 memorizes the drug solution data concerning the configuration of the drug solution C. The memory unit 33 can be configured by a RAM (Random Access Memory) and a ROM (Read Only Memory), or a PROM (Programmable ROM) such as a flash memory.

The control unit 32 is connected to the pair of electrodes (44a, 44b) and controls the operation of the drive mechanism unit 43. The control unit 32 has information processing means 32a, drive processing means 32b, and output processing means 32c. The information processing means 32a causes the memory unit 33 to memorize the drug solution data of the module 40 acquired from the terminal device 50 or the management device 60. The drive processing means 32b applies a voltage to the pair of electrodes (44a, 44b) based on the drug solution data. The drive processing means 32b has a function of determining whether or not the remaining amount of the drug solution C is equal to or less than the reference amount, based on the remaining amount information transmitted from the remaining amount sensor 48. Then, when the remaining amount of the drug solution C has become equal to or less than the reference amount, the drive processing means 32b outputs a decrease signal to indicate a decrease in the residual amount of the drug solution C to the output processing means 32c. Further, when the administration of the drug solution C is completed, the drive processing means 32b outputs an end signal indicating the end of administration of the drug solution C to the output processing means 32c.

The output processing means 32c causes the output unit 35 to output the information prompting confirmation of the remaining amount of the drug solution C, in response to the end signal from the drive processing means 32b. The output processing means 32c causes the output unit 35 to output information indicating the end of administration of the drug solution C, in response to the end signal from the drive processing means 32b. FIG. 8 shows an example in which the output unit 35 includes a light emitting means 35a including a light source such as LED (light emitting diode) and the like, and a notification means 35b including a speaker. Therefore, the output processing means 32c causes the light emitting means 35a to emit light in various modes and causes the notification means 35b to notify with sound or voice.

For example, the output processing means 32c turns on the light emitting means 35a as information for prompting the confirmation of the remaining amount of the drug solution C; and as the information indicating the end of the administration of the drug solution C, the light emitting means 35a may be let to blink. Thus, it is advisable to change the method of light emission of the light emitting means 35a according to each information. Further, the output processing means 32c informs the notification means 35b of a sound such as "the drug solution is almost exhausted" as information prompting the confirmation of the remaining amount of the drug solution C. As information indicating the end of administration of the drug solution C, it is also possible to notify the notification means 35b of a voice such as "The drug solution is exhausted" or "Please replace the module" and the like.

However, the output unit 35 may include vibration means causing vibration, or odor generating means generating certain odor, or the like. The output unit 35 may have at least one out of the light emitting means 35a, the notification means 35b, the vibration means and the odor generation means. The output unit 35 has more than two out of the light emitting means 35a, the notification means 35b, the vibration means, and the odor generating means, the output processing means 32c may operate a plurality of means in combination.

The control unit 32 can be configured with the arithmetic logic unit such as a CPU or a GPU, etc. and the drug solution administration program 33p that realizes the above-mentioned various functions working in collaboration with such arithmetic logic unit. That means, the drug solution administration program 33p is the program to make the control unit 32 and the memory unit 33 as a computer to function as the information processing means 32a, the drive processing means 32b, and the output processing means 32c.

Figure 9:
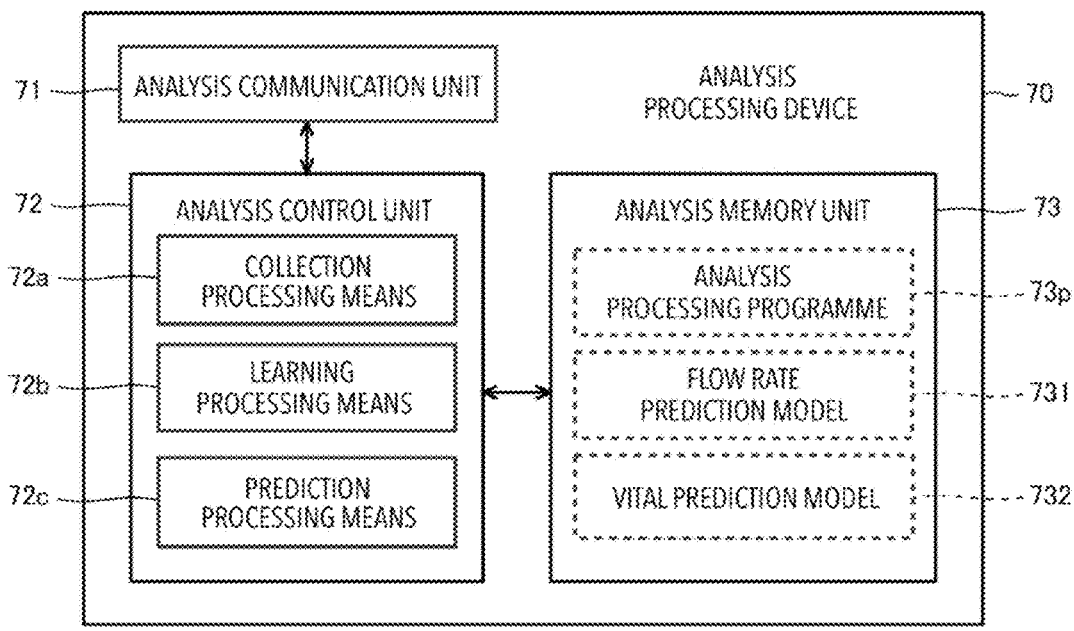
FIG. 9 is a bloc diagram illustrating the functional configuration of the analysis processing device of FIG. 1.

Next, with reference to FIG. 9, a functional configuration of the analysis processing device 70 will be described. The analysis processing device 70 includes an analysis communication unit 71, an analysis control unit 72, and an analysis memory unit 73. The analysis communication unit 71 is an interface for the analysis processing device 70 to perform wired or wireless communication with a device or the like connected to the network Ne. The analysis memory unit 73 memorizes various data in addition to the operation program of the analysis control unit 72 such as the analysis processing program 73p.

For example, the analysis memory unit 73 stores the flow rate prediction model 731 and the vital prediction model 732. The analysis memory unit 73 memorizes personal data and drug solution data for each patient. The analysis memory unit 73 can be configured by a RAM (Random Access Memory) and a ROM (Read Only Memory), a PROM (Programmable ROM), such as a flash memory, or an HDD (Hard Disk Drive), or the like.

The analysis control unit 72 has a collection processing means 72*a*, a learning processing means 72*b*, and a prediction processing means 72*c*. The collection processing means 72*a* sequentially or regularly collects the setting data for each patient and lets the analysis memory Unit 73 memorize the collected setting data.

The learning processing means 73*b* configures the flow rate prediction model 731 to predict the optimum flow rate of the drug solution C by the module 40 through machine learning based on the setting data within the analysis memory unit 73. More specifically, the learning processing means 73*b* generates the flow rate prediction model 731 by the machine learning that uses at least one of the various information included in personal data and at least one including the flow rate data among the various information included in the drug solution data. That is, the flow rate data is indispensable for generating the flow rate prediction model 731.

Further, the learning processing means 73*b* constructs a vital prediction model 732 for predicting a change in the patient's vital data by machine learning based on the setting data in the analysis memory unit 73. More specifically, the learning processing means 73*b* generates the vital prediction model 732 by machine learning using at least one of various information included in the personal data, which includes vital data, and at least one of various information included in the drug solution data, which includes flow rate data. That is, vital data and flow rate data are essential for generating the flow rate prediction model 731. However, the learning processing means 73*b* may use at least one of the pieces of information belonging to the vital data.

That is, the learning processing means 73*b* has a function extracting useful data, out of various data included in the setting data, as the feature value in machine learning. Which data out of the setting data to be used by the learning processing means 73*b* may be set in advance. Further, the learning processing means 72*b* may use, at the start of the learning, as the setting data, the entire data or most of the data stored in the analysis memory unit 73, and as the learning progresses, retain the useful data and other data may be discarded.

Here, the collection processing means 72*a* collects the setting data for each patient over time and accumulates it in the analysis memory unit 73. Therefore, the learning processing means 73*b* has the function to acquire the setting data that is freshly accumulated at the set timings, and to update the flow rate prediction model 731 and the vital prediction model 732 appropriately by making a part or all of the acquired setting data as an input.

In the present embodiment, the learning processing means 73*b* is configured to generate the flow rate prediction model 731 and the vital prediction model 732 by supervised learning using DNN (Deep Neural Network). However, the learning processing means 73*b* may generate the flow rate prediction model 731 or the vital prediction model 732 by unsupervised learning or semi-supervised learning. The learning processing means 73*b* may generate the flow rate prediction model 731 or the vital prediction model 732 by regression methods such as linear regression, logistic regression, or decision tree. Further, the leaning processing means 73*b* may generate the flow rate prediction model 731 or the vital prediction model 732 by the classification methods such as random forest or support vector machine, etc.

The prediction processing means 72*c* seeks the recommended value of the flow rate that is the prediction value of the most appropriate flow rate of the drug solution C by the module 40, by using the setting data within the preset analysis period as the input of the flow rate prediction model 731 that is a learned model generated by the learning processing means 73*b*. Further, the prediction processing means 72*c* seeks the vital prediction information that is the information to indicate the future change of the vital data of the patient by making the setting data within the preset analysis period as the input of the vital prediction model 732, that is, the learned model generated by the learning processing means 73*b*. It should be noted that the analysis period can be set from the management device 60 and can be changed as appropriate. Here, the information that the prediction processing means 72*c* seeks by using the learned model is generally called prediction data. The prediction processing means 72*c* transmits, at least one of the recommended flow rate value and the vital prediction information to the management device 60 as prediction data.

The prediction processing means 72*c* may, as the vital prediction information, seek current time-lapse data indicating prediction of change in vital data over time at current flow rate of the module 40. The prediction processing means 72*c* may, as the vital prediction information, seek the post-change time-lapse data indicating a change prediction of the vital data over time when the flow rate by the module 40 is changed into the recommended flow rate value. The prediction processing means 72*c* may seek both the current time-lapse data and the post-change time-lapse data as vital prediction information.

Further, the prediction processing means 72*c* may obtain, as the vital prediction information, the current prediction data indicating the prediction value of the vital data after the lapse of the set period at the current flow rate of the module 40. The prediction processing means 72*c* may obtain, as the vital prediction information, post-change prediction data indicating a predicted value of vital data after the set period has elapsed when the flow rate of the module 40 is changed to the recommended flow rate value. The prediction processing means 72*c* may obtain both the current prediction data and the post-change prediction data as vital prediction information.

The analysis control unit 72 can be configured with the arithmetic device such as a CPU (Central Processing Unit), a GPU (Graphics Processing Unit) or the like and an operation program, in collaboration with such arithmetic device to realize the various functions described above. That is, the analysis processing program 73*p* is a program for causing the analysis control unit 72 and the analysis memory unit 73 as a computer to function as the collection processing means 72*a*, the learning processing means 72*b*, and the prediction processing means 72*c*.

Figure 10:
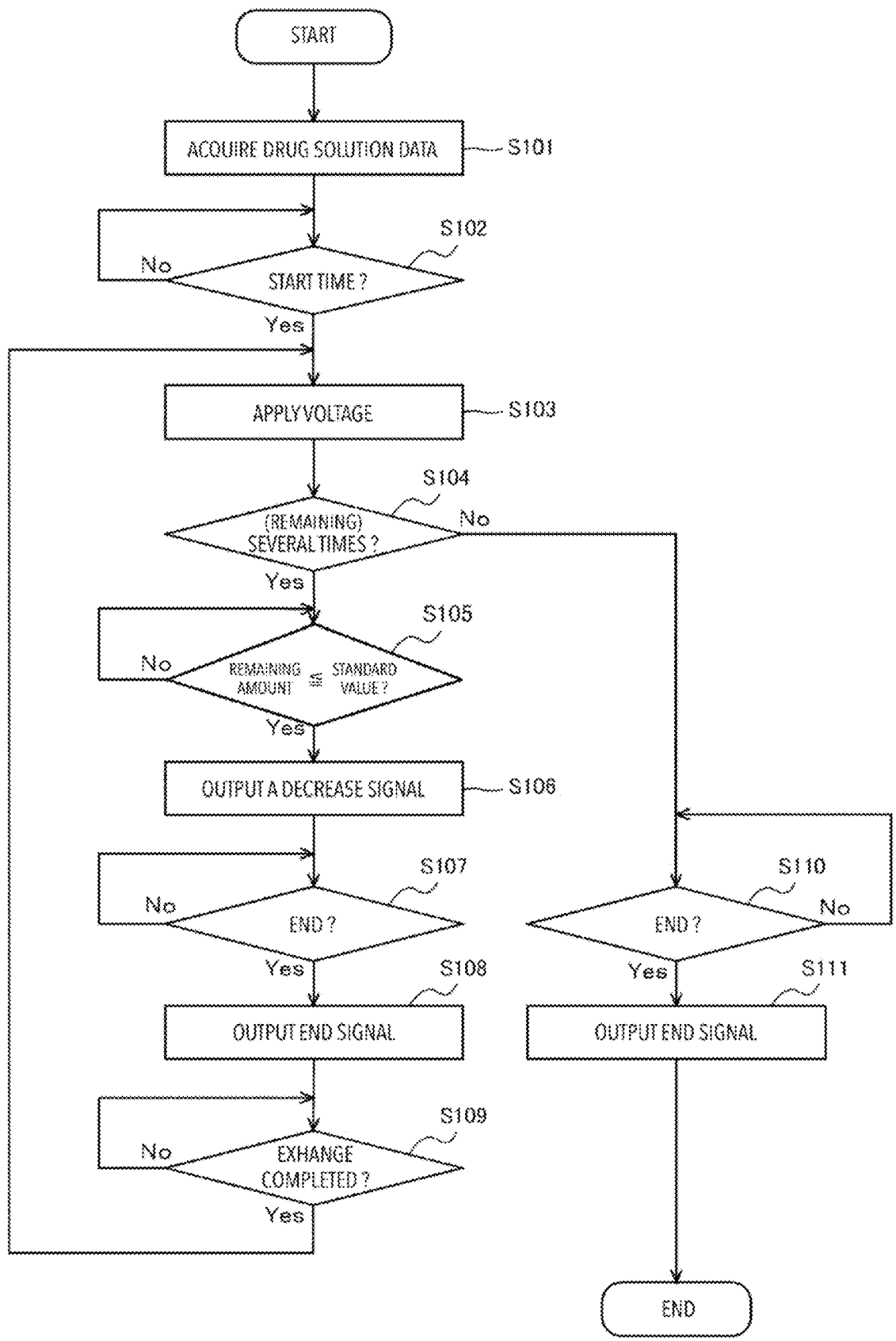
FIG. 10 is a flow chart showing the example of operation of a drug solution administration device of FIG. 1.

In continuation, in reference to the flowchart of FIG. 10, the drug solution administration method by the communication processing unit 30 of the drug solution administration device 20 will be described. First of all, the information processing means 32*a* acquires the drug solution data of the module 40 and stores the acquired drug solution data in the memory unit 33 (step S101), The drive processing means 32*b* waits till the start time of the administration of the drug solution C based on the drug solution data (step S102/No), when the start time comes (step S102/Yes), the level of voltage according to the drug solution data is applied to the pair of electrodes (44*a*, 44*b*). By doing so, after the drive solution F of the first flow path 41*b* passes through the opening of the electrode 44*a* on the upstream side, it passes through the porous body 45, passes through the opening of the electrode 44b on the downstream side, and moves towards the side of the second flow path 42b. That means, at the drive mechanism unit 43, by the movement of the drive solution F due to the electroosmotic flow, the drive force to move towards the downstream is transmitted to the drug solution C within the second flow path 42b (step S103). But, if the drive processing means 32b is, in the drug solution data, configured to commence the administration of the drug solution C immediately (step S102/Yes), a volume of a voltage corresponding to the drug solution data is to be applied immediately (step S103).

When the number of repetitions of administration of the drug solution C by the module 40 is set to a plurality of times two times or more) in the drug solution data (step S104/Yes), the drive processing means 32b obtains the residual amount information from the residual amount sensor 48. It is acquired and it is determined whether the remaining amount of the drug solution C is equal to or less than the reference amount (step S105). The drive processing means 32b waits until the residual amount of the drug solution C becomes equal or less than the reference amount (step S105/No), and when the residual amount of the drug solution C becomes equal or less than the reference amount (step S105/Yes), releases a drop signal to the output processing means 32c. The output processing means 32c causes the output unit 35 to put outputs, according to a decrease signal, information prompting confirmation of the remaining amount of the drug solution C (step S106).

And the drive processing means 32b waits till the administration of the drug solution C ends (step S107/No), and when the administration of the drug solution C ends (step S107/Yes), it outputs the end signal to the output processing means 32c. The output processing means 32c causes the output unit 35 to output information indicating the end of administration of the drug solution C in response to the end signal (step S108).

The drive processing means 32b waits till the module 40 is replaced (step S109/No), and when the module 40 is replaced (step S109/Yes), the process proceeds to the step S103. It should be noted that after the second time in the step S104, the drive processing means 32b determines whether the remaining number of the administrations of the drug solution C is a plurality of times.

On the other hand, when the number of times the module 40 repeats administrating the drug solution C is set to 1 in the drug solution data of the drive processing means 32b (step S104/No), the drive processing means 32b waits till the administration of the reference amount of the drug solution C is exhausted (step S110/No). The drive processing means 32b outputs an end signal to the output processing means 32c when the administration of the prescribed amount of the drug solution C is completed (step S110/Yes). The output processing means 32c causes the output unit 35 to output information indicating the end of administration of the drug solution C in response to the end signal (step S111).

It should be noted that normal drug solution administration is completed with one module 40 since the module 40 can be allowed to keep required amount for the drug solution administration in normal circumstances. Therefore, the number of times the module 40 repeats administration of the drug solution C does not have to be set as a setting item of the drug data.

Figure 11:
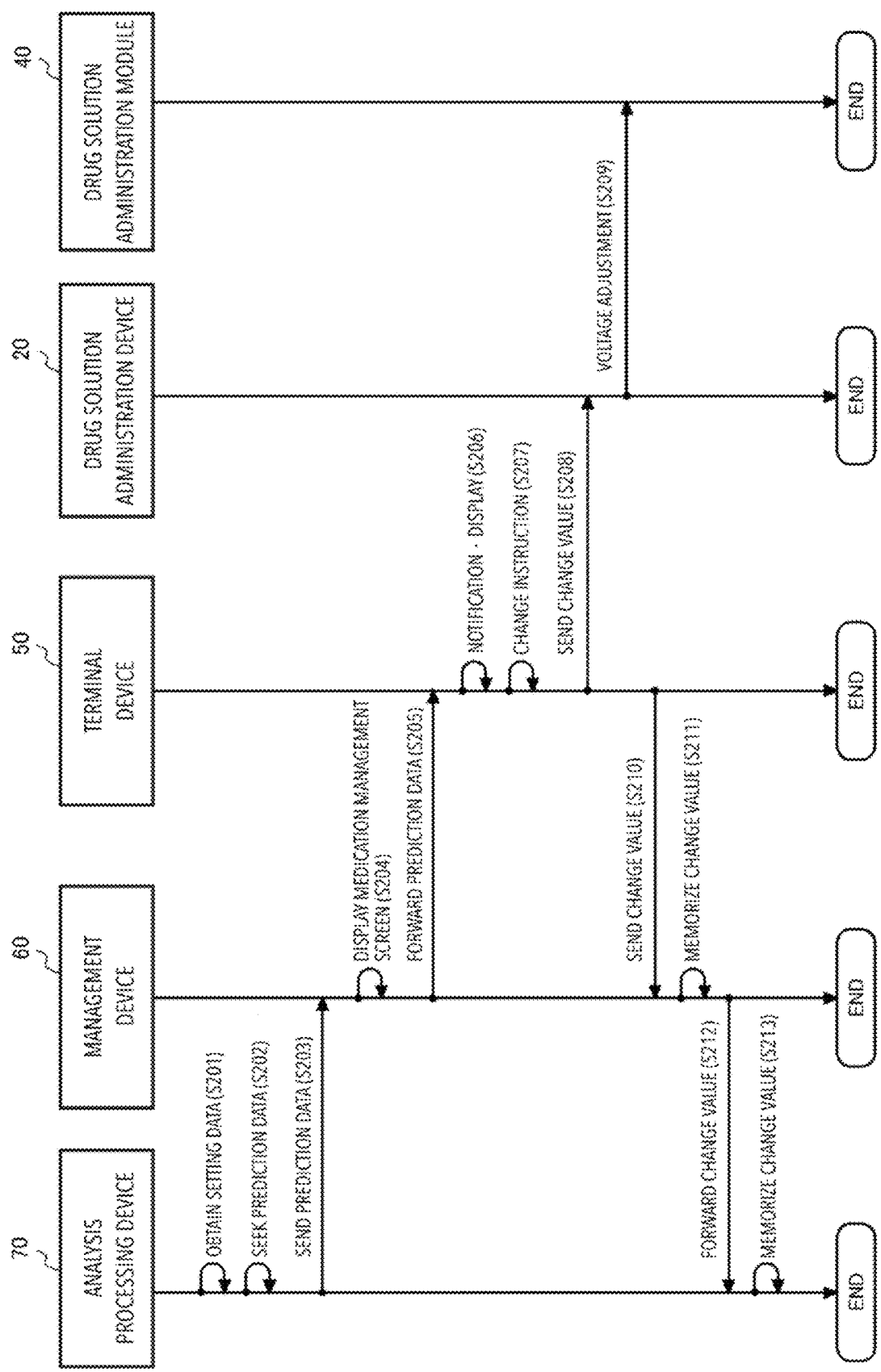
FIG. 11 is a sequence chart illustrating the flow of operations of the medication management system of FIG. 1.

Next, with reference to FIG. 11 and FIG. 12, an example of a medication management method by the medication management system 100 will be described. Here, out of the processes concerning the medication management method, the process of pre-processing of machine learning is omitted. It should be noted that, in the present specification, "medication" means administration of a liquid medicine.

First, the prediction processing means 72c of the analysis processing device 70 acquires the setting data from the analysis memory unit 73 (step S201). Next, the prediction processing means 72c obtains the prediction data by making the acquired setting data as an input to both the flow rate prediction model 731 and the vital prediction model 732. FIG. 11 and FIG. 12 are examples where the prediction processing means 72c seeks as the flow rate data both the recommended flow rate value and the vital prediction information (step S202). The prediction processing means 72c transmits the calculated prediction data to the management device 60 (step S203).

Figure 12:
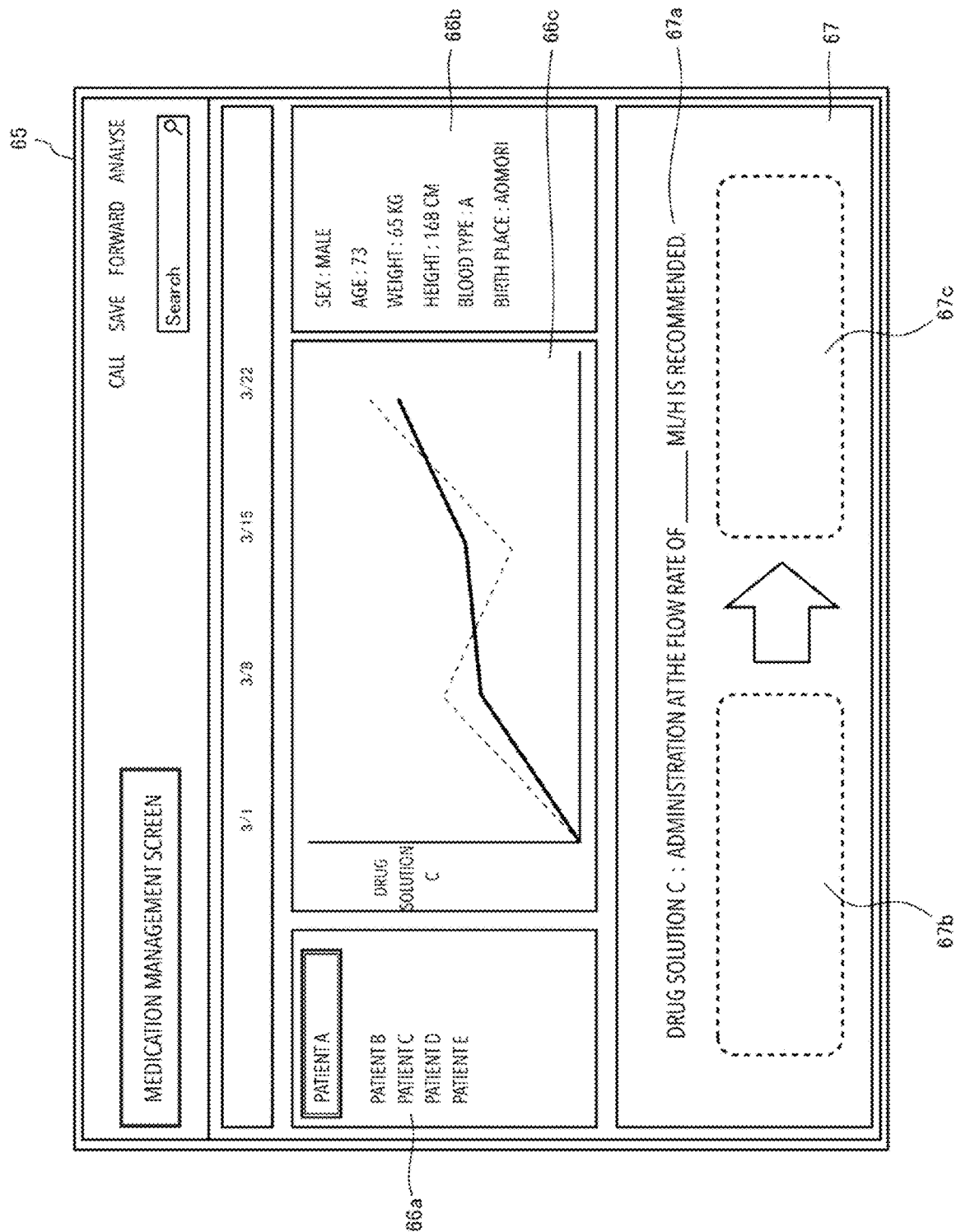
FIG. 12 is an explanatory drawing illustrating the medication management screen displayed at the display unit of the management device of FIG. 5.

The display processing means 62b of the management device 60 causes the display unit 65 to display the medication management screen as described in FIG. 12 based on the prediction data and the like transmitted from the analysis processing device 70. For example, the display processing means 62b causes the sub-window or the like to display information indicating that the prediction data has been transmitted along with an instruction button to instruct the display of the medication management screen, and when the instruction button is pressed, the medication management is displayed (step S204).

The medication management screen of FIG. 12 includes a patient's selection column 66a that receives patient's selections, an attribute display column 66b that displays the attribute data of each patient, and a flow rate display column 66c that indicates the transition of the flow rate of the drug solution C in comparison with its past. Further, the medication management screen has the prediction column 67 where the information based on the prediction data is displayed. The prediction column 67 as illustrated in FIG. 12, has the recommended information 67a that includes the recommended flow rate, the current prediction unit 67b, and the post-change prediction unit 67c. The display processing means 62b displays the information based on at least either one of the current status time-lapse data and the current status prediction data, and the post-change prediction unit 67c displays the information based on at least either one of the post-change time-lapse data and the post-change prediction data. By doing so, the user can grasp the change of vital data at a glance in case the flow rate of the drug solution C is changed to the recommended flow rate value.

Further, the information processing means 62a of the management device 60 transfers the prediction data transmitted from the analysis processing device 70 to the terminal device 50 (step S205). When the prediction data is transmitted, the display processing means 52b of the terminal device 50 causes the notification unit 55 to output an alert and causes arrival information prompting confirmation of the recommended flow rate value to be displayed on the terminal display unit 54b in a sub window or the like. When the display of the recommended flow rate is instructed by touching the sub window or the like, the display processing means 52b causes the terminal display unit 54b to display the flow rate adjustment screen in which the recommended flow rate is displayed on the screen as shown in FIG. 7, for example. As a result, the current flow rate of the chemical liquid C can be changed to the recommended flow rate value by a simple operation (step S206).

That is, when the user instructs to change the flow rate on the flow rate adjustment screen (step S207), the communication processing means 52a transmits a change value that indicates the post-change flow rate to the drug solution administration device 20 (step S208). The drive processing means 32*b* of the drug solution administration device 20 adjusts the applied voltage to the pair of electrodes (44*a*, 44*b*) to become the voltage corresponding to the change value (step S209).

Also, the communication processing means 52*a* transmits the change value to the management device 60 (step S210). The information processing means 62*a* of the management device 60 gets the management memory unit 63 memorize the change value transmitted from the terminal device 50 as the current flow rate (step S211), and, at the same time, transfers it to the analysis processing device 70 (step S212). The collection processing means 72*a* of the analysis processing device 70 causes the analysis memory unit 73 to memorize the change value sent from the management device 60 as the current flow rate (step S213).

Vital data, external data and the like may change from moment to moment, and along with this, the recommended flow rate value can change significantly. In this regard, the medication management system 100 can quickly follow the change of the recommended flow rate value according to the change in vital data, external data and the like by performing the process of steps S206 to S209. It should be noted that the display processing means 52*b* may do the processing of the step S206 only when the difference between the current flow rate value and the recommended flow rate value is larger than the preset threshold value.

As above, in the drug solution administration module 40 according to the first embodiment, the connecting flow path that connects the downstream end of the first flow path 41*b* and the upstream end of the second flow path 42*b* is formed at the porous body 45 and the pair of electrodes (44*a*, 44*b*) that sandwiches it. And, the second flow path 42*b* is connected to the branch path of the drug solution administration device 20 and the downstream side of the branch path 22*a* is connected to the main path 22*c* connected to the tube 85 for infusion. Therefore, because of the generation of the electroosmotic flow due to the potential difference between the pair of electrodes (44*a*, 44*b*), the drive solution F permeated into the porous body 45 flows towards the downstream side through the connecting flow path. Hence, according to the applied voltage to the pair of electrodes (44*a*, 44*b*) the drug solution C within the second flow path 42*b* is pushed out immediately towards the downstream side, so that the quick and safe administration of the drug solution can be realized without hassles. As for the drive mechanism unit 43, when the drive solution F that flows into the porous body 45 is exhausted, in principle, the electroosmotic flow does not occur, and the drive is halted if the drive solution F within the first flow path 41*b* is exhausted. Therefore, by making the amount of the drive solution F that fills the drug solution administration module 40 reduced only by the adjusted amount compared to the amount of the drug solution C, the drug solution administration module 40 can mechanically ensure the safety without making such function as communication and control intervene.

The drug solution administration device 20 is connected to the pair of electrodes (44*a*, 44*b*), and has the control unit 32 that controls the operation of the drive mechanism unit 43. Therefore, the drug solution administration module 40 can be configured without a control device such as a CPU or the like, and can be manufactured at low cost. Further, since each component of the drug solution administration module 40 is made of the combustible material, it can be disposed as combustible waste. That is, the drug solution administration module 40 is an environmentally friendly module and, from the point of its cost, can be suitably used as a disposable module. In addition, by using the drug solution administration module 40, as it aims to miniaturize its pump and save power, and vibration, pulsatile flow, and noise can be suppressed, so that the reliability of the pump can be enhanced.

By the way, an unexpected interruption of the administration of the drug solution C may be life-threatening for the patient. Therefore, a stable operation of the pump used for administering the drug solution C is expected. In this regard, the drive mechanism unit 43 that functions as an electroosmotic flow pump can push the drug solution C into the main path 22*c*, even though some air is included in the first flow path 41*b* and the second flow path 42*b*, because its drive force as a pump, that is, the power of pushing out the liquid is strong, as compared with a syringe pump. Therefore, it is possible to avoid the situation where the administration of the drug solution C is delayed, it is possible to enhance its credibility as a medical equipment.

And, in the existing infusion system, a medical worker may be to a drug while diluting a drug solution or setting the drug solution in a syringe, which is a safety issue. In this regard, in the drug solution administration unit 10 completes preparation for drug solution administration only by setting the module 40 in which the drug solution C is injected in advance in the drug solution administration device 20, the preparation of the drug solution administration is complete, the risk of exposing health care workers to drugs can be reduced and the safety can be enhanced. In addition, patient's vital data can be stored, sequentially or regularly, in the analysis processing device 70, and checked any time from the management device 60. Therefore, health care workers, etc., can check the change of the vital data, etc., after the drug solution administration, and thus the effectiveness of the drug solution administration can be verified.

Here, pressor can be administered during infusion at the time of emergency care such as the heart disease, but the key to the treatment is to increase or decrease its flow rate according to the condition of the patient. However, it is difficult to increase or decrease the flow rate by operating a syringe pump by health care workers. On the other hand, the drive mechanism unit 43, that functions as the electric vibration flow pump, can materialize the administration of extremely small amount of the drug solution and, at the same time, from the management device 60 or the terminal device 50, easily change the flow rate of the drug solution C. Therefore, the credibility and safety of the treatment can be enhanced.

The analysis processing device 70 analyzes the personal data that includes the information on the attributes of the patient and the drug solution data that includes the information of the flow rate of the drug solution of the module 40. And, the display unit 65 of the management device 60 displays information based on the analysis result by the analysis processing device 70. That is, according to the medication management system 100, external analysis result of the personal data and the drug solution data can be confirmed by the management device 60 placed in a medical setting or the like.

In the first embodiment, the learning processing means 72*b* generates, by the machine learning based on the past setting data, the flow rate prediction model 731 and the vital prediction model 732. And, the prediction processing means 72*c* seeks the prediction data by considering the setting data during the period of analysis as the input of the flow rate prediction model 731 or the vital prediction model 732. More specifically, the analysis processing device 70 seeks the recommended flow rate value by using the personal data or the drug solution data. The display unit 65 displays the recommended information 67*a* that includes the recommended flow rate value, in the aspect as described in FIG. 12, for example. Therefore, those who are health care workers, etc., can grasp at a glance whether the change of the flow rate is necessary or not, and by changing the flow rate corresponding to the recommended information 67*a*, can enhance the efficiency of the treatment. That is, it is possible to reduce the burden on the part of a medical staff or the like in adjusting or setting the medical conditions of medication and able to let the medication efficiently perform under the accurate conditions.

The analysis processing device 70 may seek the vital prediction information that shows the future change of the vital data of the patient by using the personal data including the vital data of the patient and the drug solution data. It would be good if the display unit 65 shows the information based on the vital prediction information. For example, as the vital prediction information, at current flow rate of the module 40, there are current time-lapse data that indicates the prediction value of the vital data after the set period had elapsed. Further, as the vital prediction information, in the case the flow rate of the module 40 is changed to the recommended flow rate, there are the post-change time-lapse data that indicates the prediction of change of vital data over time and the post-change prediction data that indicates the predicted value of vital data after the set period has elapsed.

The information based on current time-lapse data and the current prediction data is, for example, displayed in the current prediction unit 67*b* of FIG. 12, and the information based on the post-change time-lapse data and the post-change prediction data is, for example, displayed on the post-change prediction unit 67*c* of FIG. 12. From the information based on the current time-lapse data, the prediction of change of the vital data at current flow rate can be confirmed, and, from the information based on current prediction data, the predicted value of the vital data at a certain point of time in future at current flow rate can be confirmed. Therefore, the adjustment of the flow rate of the drug solution C, the improvement of eating habits, and correcting lifestyle can be realized. Also, from the post-change time-lapse data and the post-change prediction data, the credibility of the recommended flow rate value can be confirmed. If the comparison between the information based on the current prediction data and the information based on the post change prediction data, or the comparison between the information based on the current time-lapse data and the information based on post-change time-lapse data can be displayed as in FIG. 12, it is possible to let the user recognize the merit gained by adjusting the flow rate. The display processing means 62*b* may be displayed on the display unit 65 with a graph overlaying the information based on current time-lapse data and the information based on the post-change time-lapse data.

Modification Example 1a

Figure 13:
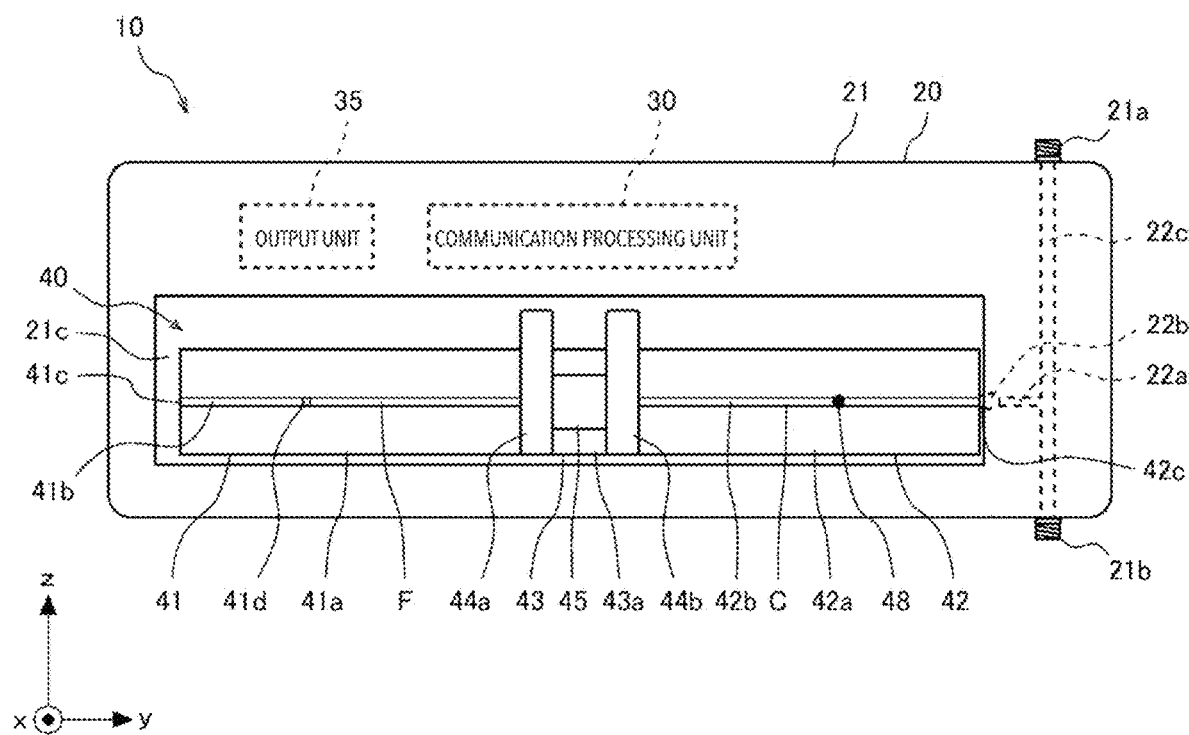
FIG. 13 is a diagram illustrating a drug solution administration unit according to the Modification 1a of Embodiment 1 the present invention.

With reference to FIG. 13, the drug solution administration unit 10 according to this modification example 1a will be described. In the drug solution administration unit 10 of modification example 1a, the direction in which the module 40 is mounted on the drug solution administration device 20 is different from the direction shown in FIG. 4. That is, in the module 40 is arranged in the containment unit 21*c* such that the first flow path 41*b* and the second flow path 42*b* are parallel to the bottom surface of the drug solution administration device 20. When the length in the bending direction (the direction of x-axis) is longer than the length in the thickness direction (the direction of z-axis) as in the module 40 illustrated in FIGS. 2 and 3, the safety level is higher when the module 40 is placed in the containment unit 21*c*, and the length in the height direction of the drug solution administration device 20 can be shortened.

Modification Example 1b

The medication management system 100 according to modification example 1b is characterized by the configuration related to machine learning of the analysis processing device 70. The learning processing means 73*b* of the present modification example 1b establishes the analysis prediction model for delivering the effects and the side-effect when the flow rate by the module 40 is changed to the recommended flow rate value by machine learning based on the setting data within the analysis memory unit 73. For generation of the analysis prediction model, vital data and flow rate data are mandatory. This is because the effects and the side-effects appear in the change of the vital data. Therefore, the prediction processing means 72*c* of this modification example 1b can seek the effects and the side-effects, as the prediction data when the flow rate by the module 40 is changed to the recommended flow rate value by making the setting data acquired from the analysis memory unit 73 as the input of the analysis prediction model.

Figure 14:
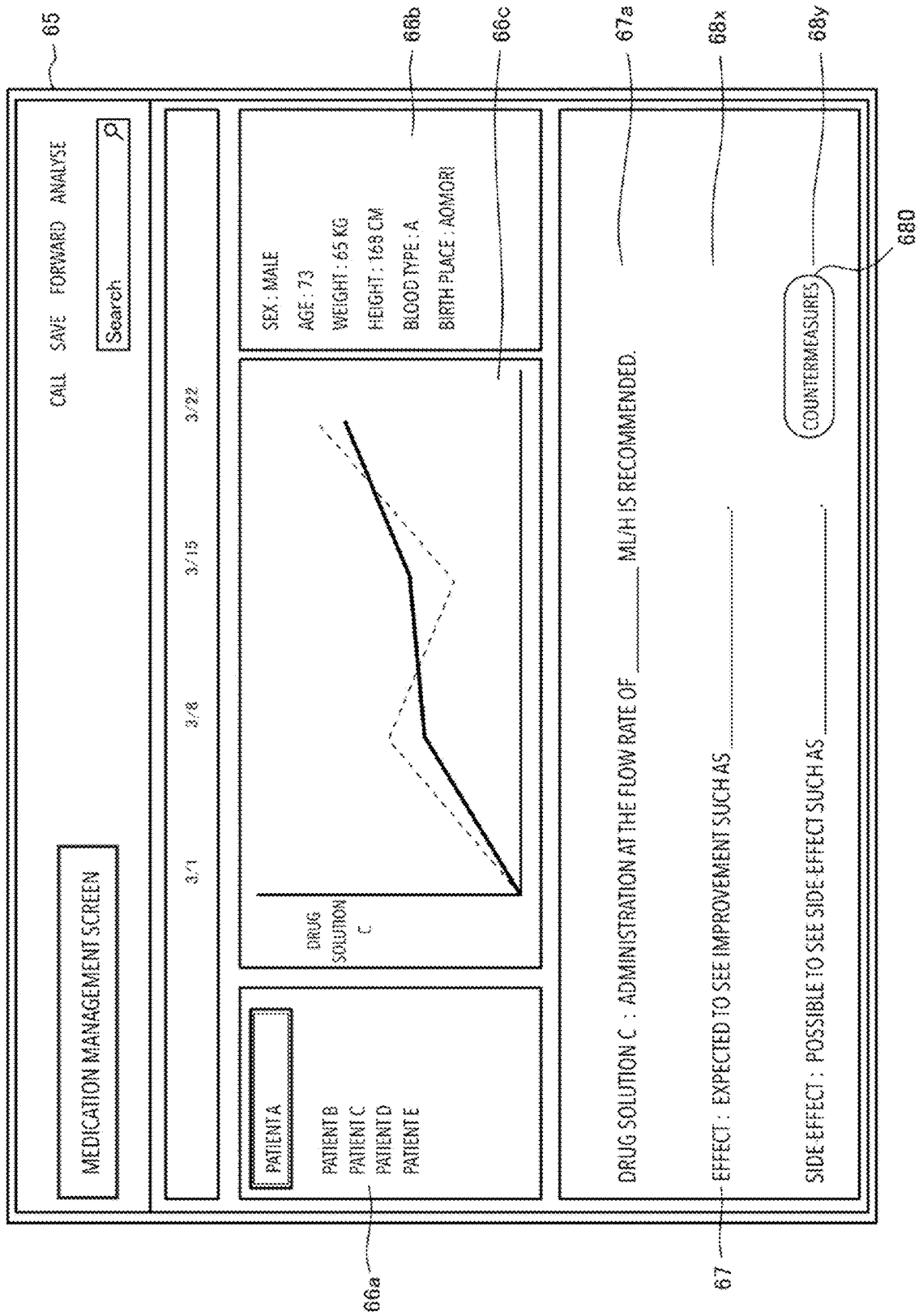
FIG. 14 is an explanatory drawing illustrating the medication management screen displayed on the display unit of the management device according to the Modification 1b of Embodiment 1 of the present invention.

In the present modification example 1b, the display processing means 62*b* of the management device 60 causes the display unit 65 to display a medication management screen as illustrated in FIG. 14 based on the prediction data and the like transmitted from the analysis processing device 70. The prediction column 67 of the medication management screen of FIG. 14 has the effect information 68*x* indicating an effect and the side-effect information 68*y* indicating a side-effect together with recommendation information 67*a* including a recommended flow rate value. The display processing means 62*b* may, as shown in FIG. 14, get the countermeasure key 680 for transitioning to the page indicating the countermeasures displayed in association with the side-effect information 68*y*.

But the analysis control unit 72 may, by statistically analyzing the setting data or the vital prediction information and the like, have the analytical means to calculate the effects and the side-effects when the flow rate by the module 40 is changed to the recommended flow rate value. Also in this case the display processing means 62*b* can display the medication management screen as shown in FIG. 14 on the display unit 65 by transmitting the result of analysis by analytical means to the management device 60.

Second Embodiment

Figure 15:
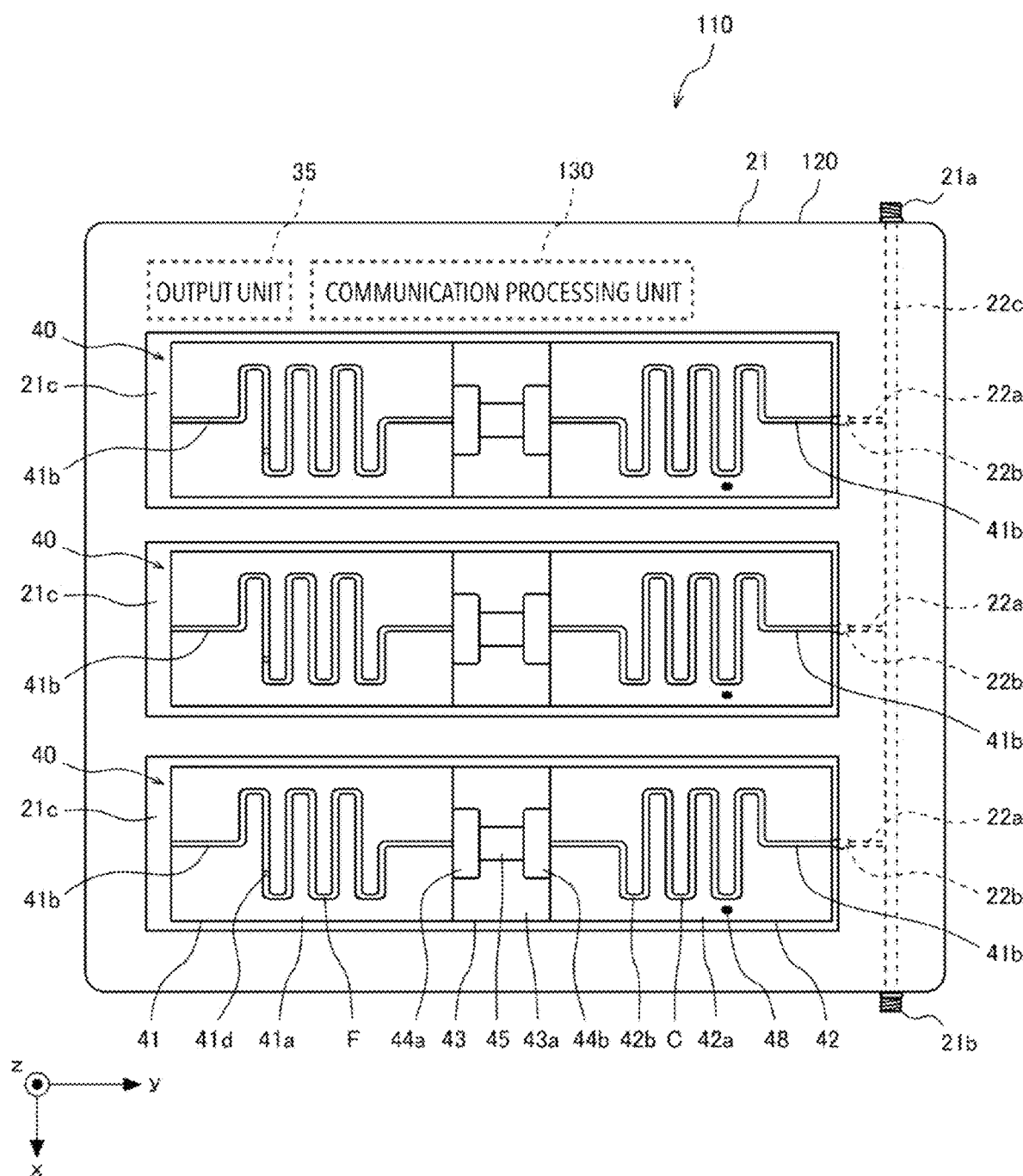
FIG. 15 is an explanatory drawing illustrating the external appearance of the drug solution administration unit according to Embodiment 2 of the present invention.

With reference to FIG. 15, the configuration of the drug solution administration unit 110 of the second embodiment will be described. Since the overall configuration of the medication management system 100 according to the second embodiment is similar to that of the first embodiment, a configuration different from that of the first embodiment will be particularly described. The same configuration components as those in the first embodiment described above are designated by the same reference numerals and description thereof will be omitted.

The drug solution administration device 120 has a configuration in which a plurality of modules 40 can be mounted. That is, the drug solution administration device 120 has a plurality of the containment unit 21c, and a plurality of the branch paths 22a connected to the main path 22c are provided in a one-to-one correspondence with each containment unit 21c. A flow path connecting unit 22b is provided at the upstream end of each branch path 22a. That is, the drug solution administration device 120 has a plurality of flow path connecting units 22b and a plurality of the drug solution administration modules 40 mounted therein.

Figure 4:
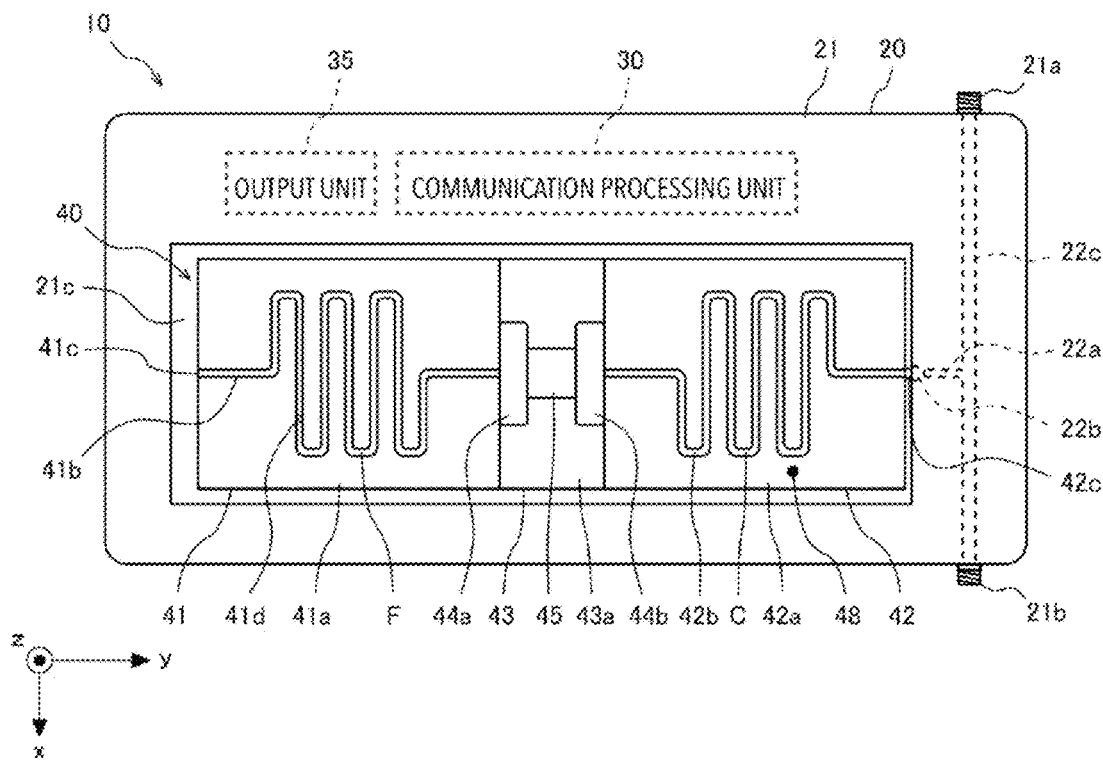
FIG. 4 is a diagram illustrating the external appearance of the drug solution administration unit of FIG. 1.

FIG. 15 illustrates a drug solution administration device 120 in which three module 40 can be mounted, and each module 40 is arranged in the same orientation as in FIG. 4. However, the plurality of modules may also be arranged in the orientation as shown in FIG. 13, and at least one or a plurality of modules 40 may be arranged in a different orientation from the rest of the modules 40. When such a configuration is adopted, the shape of the containment unit 21c may be adjusted according to the arrangement of the modules 40. It should be noted that the partition between the two containment units 21c is not limited to the mode shown in FIG. 15. For example, the housing 21 may have one containment unit 21c capable of housing a plurality of modules 40 and may have two partitions extended from the rear wall.

The communication processing unit 130 has power supply terminals that are individually connected to each terminal of the pair of electrodes (44a, 44b) of the plurality of modules 40. That is, the control unit 32 of the communication processing unit 130 is configured to individually control the operation of the plurality of modules 40 mounted on the drug solution administration device 120. The other configuration of the communication processing unit 130 is the same as that of the communication processing unit 30 of the first embodiment.

Next, with reference to FIG. 16, a setting pattern relating to operation control of the plurality of modules 40 will be described. The setting regarding the operation control of the plurality of modules 40 is basically performed by the management device 60. The pattern set by the management device 60 becomes the control pattern when the control unit 32 of the drug solution administration device 120 controls the operation of the plurality of modules 40 as it is.

First, the continuous pattern is a pattern in which one or a plurality of modules 40 are continuously operated. FIG. 16 shows an example in which the modules 40 are continuously operated one by one. The management device 60 can be set to sequentially switch and administer different drug solutions C1 to C3 as in (1) and to continuously administer the same drug solution C as in (2). Since a plurality of modules 40 can be mounted on the drug solution administration device 120, the occurrence of the time lag at the time of replacing the module 40 can be prevented by setting a continuous pattern. In addition, since there is always an empty containment unit 21c (the containment unit 21c in which the stopped module 40 is accommodated or the module 40 is removed), in principle, continuous administration of the drug solution C can be realized permanently. It is to be noted that with the drug solution administration device 120 capable of mounting the four modules 40 the modules 40 can be continuously operated two by two, which is effective when the administration volume needs to be increased or when a plurality of different types of drug solution C needs to be continuously administered.

Next, the intermittent pattern is a pattern in which after the operation of one or a plurality of modules 40 is completed, the operation of the next one or a plurality of modules 40 is started after waiting a preset waiting time W. During the waiting time W, only the infusion Y will be administered to the patient. It is effective when it is desired to avoid mixing different drug solutions C during continuous administration of the drug solution C, or when it is desired to provide a time lag in administration of the drug solution C in order to reduce the burden on the patient. A pattern similar to the intermittent pattern can be realized by the drug solution administration device 20 according to the first embodiment, but the replacement of the module 40 does not have to be done as many times as the number of mountable modules 40, hence the drug solution administration device 120 has an advantage. It should be noted that as (1) and (2) are the same as the continuous pattern.

Next, the simultaneous pattern is a pattern in which the plurality of modules 40 are simultaneously operated. For example, in the management device 60, as (1), it is possible to perform a setting such that the plurality of modules 40 corresponding to the drug solutions C1 to C3 all different from each other are simultaneously operated. Further, in the management device 60, as in (2), it is possible to perform a setting for simultaneously operating a plurality of modules 40 corresponding to the same drug solution C1 and one or a plurality of modules 40 corresponding to a different drug solution C2. Further, in the management device 60, as in (3), it is possible to perform the setting for simultaneously operating the plurality of modules 40 all corresponding to the same drug solution C.

Subsequently, the compensating pattern is a pattern in which one or more modules are operated and other modules 40 are appropriately operated according to the movement of the vital data or an instruction from the analysis processing device 70 or the management device 60. The compensating pattern can be set in advance according to past trends or analysis, prediction and the like in the analysis processing device 70, but the terminal device 50 may automatically transmit a control signal to the drug solution administration device 120 according to the instructions from the management device 60 or the like.

The management device 60 can individually set the flow rates of the plurality of modules 40 in any of the patterns. Therefore, especially when a plurality of modules 40 corresponding to different drug solutions C are simultaneously operated, the mixing ratio of the drug solution C can be finely adjusted. Further, in the management device 60, various settings can be performed by combining each of the patterns as mentioned above.

Figure 16:
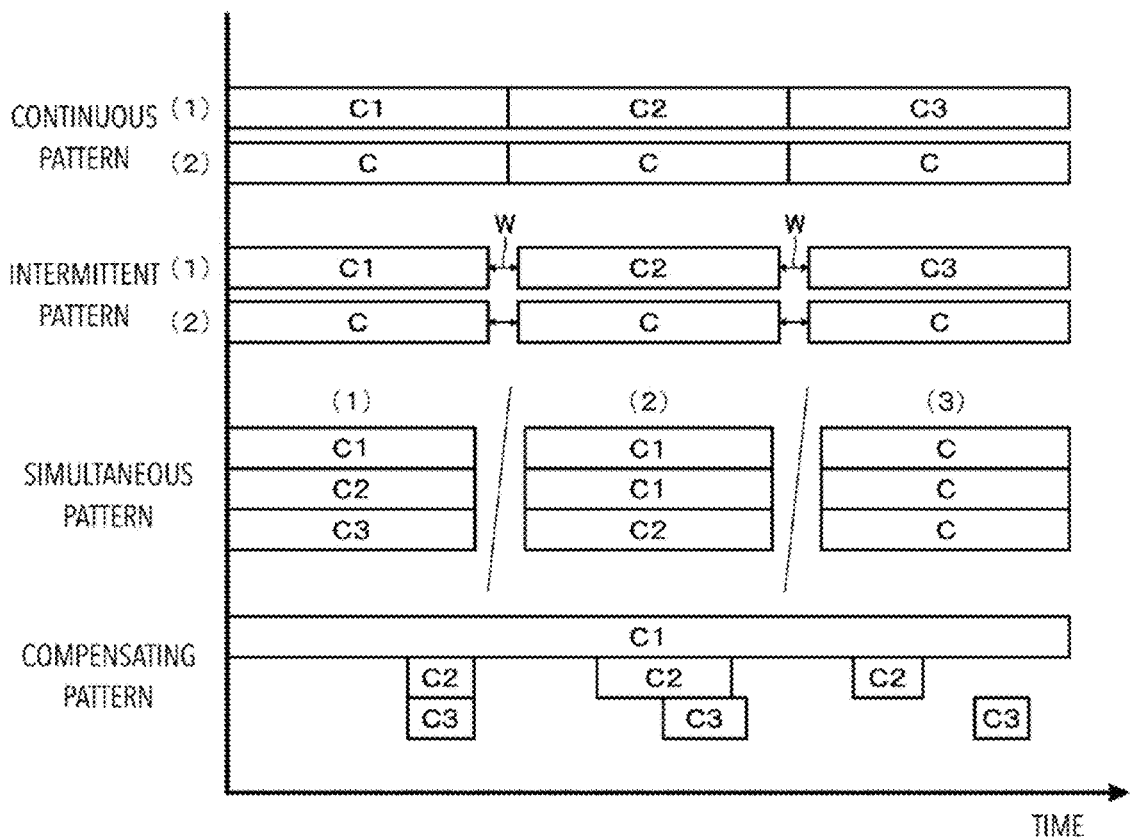
FIG. 16 is an explanatory drawing illustrating the setting pattern concerning the administration of the drug solution of the drug solution administration unit of FIG. 15.

In FIG. 16, a pattern of the drug solution administration device 120 capable of mounting the three modules 40 is illustrated for description in association with the configuration of FIG. 15, but the pattern is not limited to this. That is, the pattern of the drug solution administration device 120 that can mount two modules 40 and the pattern of the drug solution administration device 120 that can mount four or more modules 40 are the same as those in FIG. 16, and various patterns can be combined to set various settings. It should be noted that the above-mentioned settings concerning the operation control of the plurality of modules 40 may be executed by the terminal device 50.

The management device 60 transmits the setting contents related to the operation of the plurality of modules 40 to the communication processing unit 30 via the terminal device 50. That is, the management device 60 transmits the flow rate data indicating the flow rate of the drug solution administration by the plurality of modules 40 and the administration data indicating the timing of the drug solution administration by the plurality of modules 40 to the communication processing unit 30 via the terminal device 50. The administration data includes at least one out of information indicating the order of administration and information indicating the time zone of administration (start time and end time of the administration).

The drive processing means 32b of the control unit 32 controls the operation of the drive mechanism unit 43 of each module 40 based on the flow rate data and the administration data transmitted from the management device 60. The drive processing means 32b has a continuous administration function of continuously administering the drug solution C in the plurality of modules 40. The continuous administration function corresponds to the continuous pattern of FIG. 16. The drive processing means 32b has a simultaneous administration function of simultaneously administering the drug solution in two or more modules 40. The simultaneous administration function corresponds to the simultaneous pattern and the compensating pattern of FIG. 16. It should be noted that in the case of the drug solution administration device 120 capable of mounting four or more modules 40, the simultaneous administration function corresponds to the continuous pattern and the intermittent pattern of FIG. 16. The drive processing means 32b has an intermittent processing function that starts the administration of the drug solution in the other one or the plurality of modules 40 after the administration of the drug solution in the one or the plurality of modules 40 is completed and the predetermined waiting time W has elapsed. The intermittent processing function corresponds to the intermittent pattern of FIG. 16.

Figure 17:
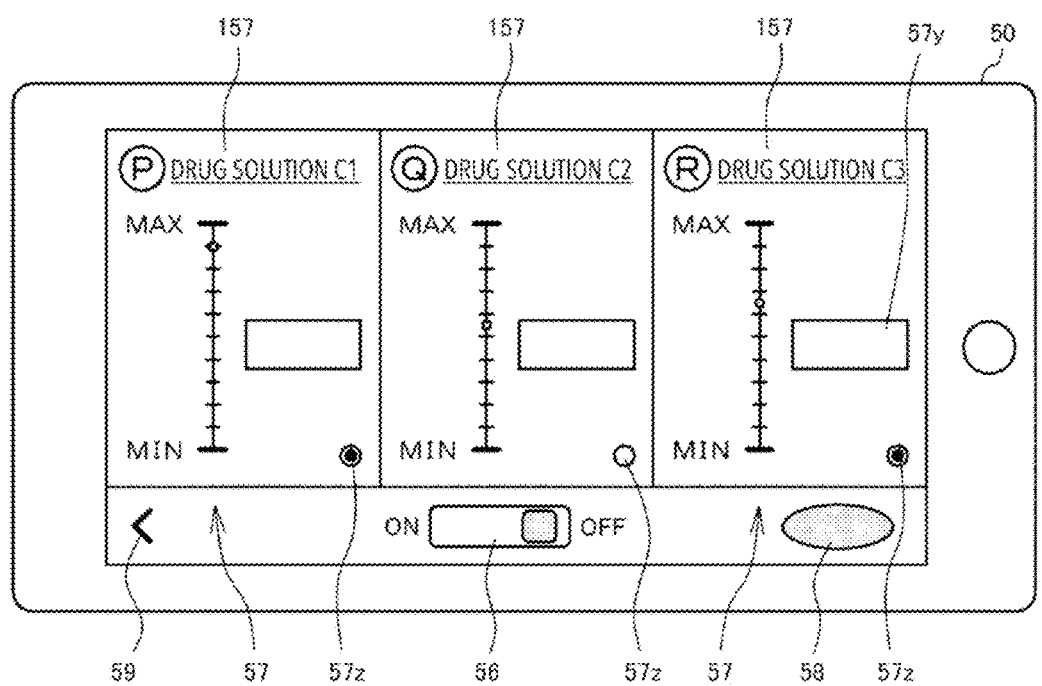
FIG. 17 is an explanatory drawing illustrating the confirmation operation screen displayed at the display unit of a terminal device according to a second embodiment of the present invention.

Here, the confirmation operation screen displayed on the terminal display unit 54b of the second embodiment will be described with reference to FIG. 17. Regarding the same components as those of the confirmation operation screen of FIG. 7, explanation is omitted by assigning same reference numerals. The confirmation operation screen is a screen for confirming the state of the drug solution administration unit 110 and adjust the flow rate. The display processing means 52b displays a device information input screen in response to a user operation. When a device information of the drug solution administration device 120 is input on the input screen and the display of the confirmation operation screen is instructed, the display processing means 52b displays the confirmation operation screen as shown in the FIG. 17 on the terminal display unit 54b.

The confirmation operation screen according to the second embodiment has a configuration in which each flow rate of the plurality of modules 40 can be individually confirmed and changed. Here, the upper module 40 in FIG. 15 corresponds to the area P' in FIG. 17, and the middle module 40 corresponds to the area 'Q' in FIG. 17 and the lower module 40 corresponds to the area 'R' in FIG. 17. In each area, the names of the drug solution (drug solutions C1 to C3) corresponding to the modules 40 are shown in the respective areas.

Though the reference numerals are omitted, since the cursor 57x of each slide bar 57 is different, it is possible to confirm that the flow rate in each module 40 is set to a different value. By visually recognizing the status display unit 57z in each area, it can be confirmed that the upper module 40 and the lower module 40 are being driven, and the interrupted module 40 is being stopped. The processing content of the control unit 32 according to the other configuration and the operation on the confirmation operation screen is the same as the content described with reference to FIG. 7.

Next, in reference to FIG. 18, the medication management screen displayed on the display unit of the management device 60 according to the second embodiment will be described. The display processing means 62b has a function of visually displaying on the display unit 65 all data handled by the medication administration system 100, such as personal data of a plurality of patients, analysis data and prediction data by machine learning and the like. The medication management screen of FIG. 18 is an example thereof.

Figure 18:
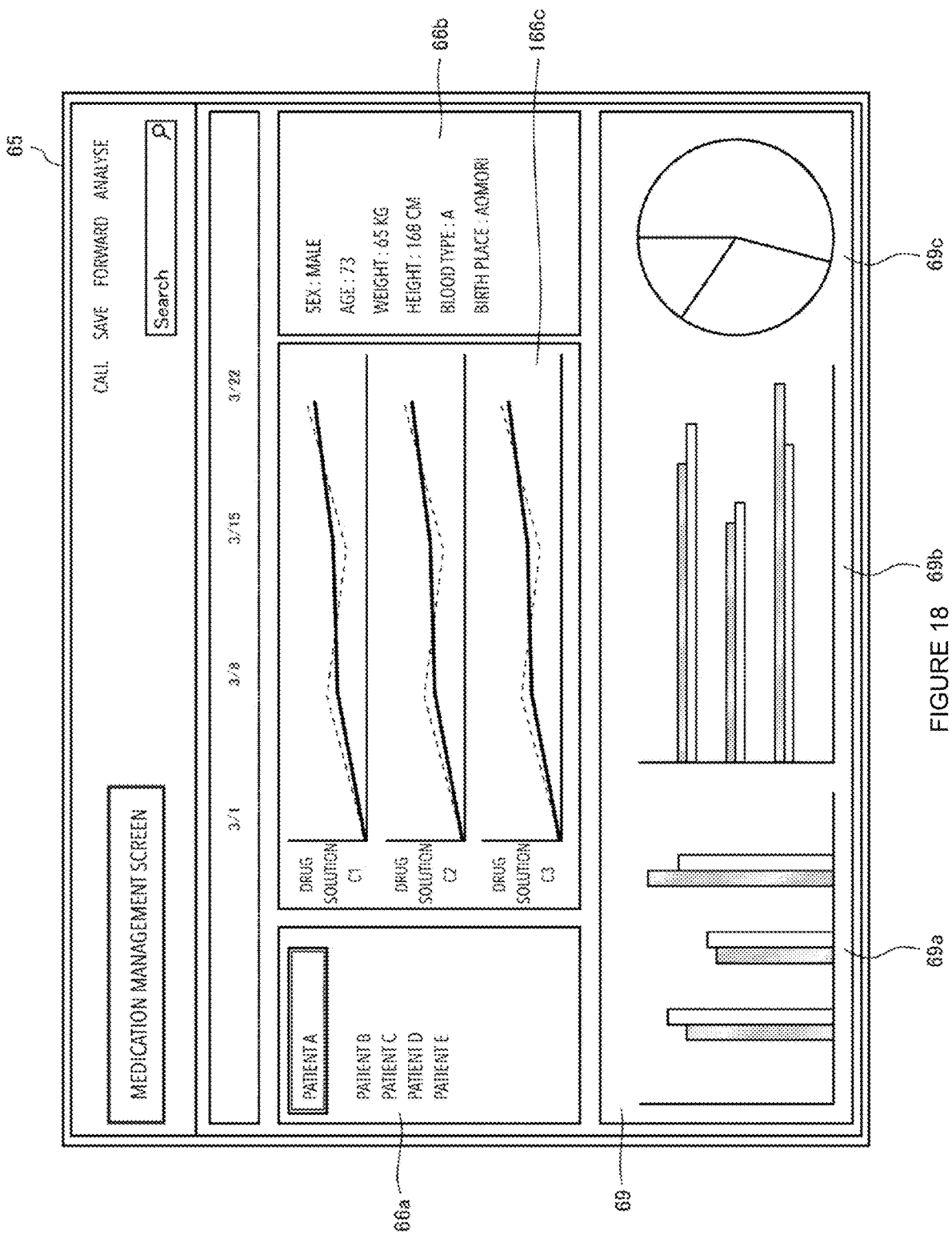
FIG. 18 is an explanatory drawing showing the medication management screen displayed at the display unit of a management devise according to Embodiment 2 of the present invention.

The display processing means 62b causes the display unit 65 to display a medication management screen as illustrated in FIG. 18 based on the prediction data and the like transmitted from the analysis processing device 70. The flow rate display column 166c displays a graph indicating the transition of each flow rates of the drug solutions C1 to C3 in comparison with the past. The status display column 69 includes a cumulative information unit 69a indicating cumulative usage status of each drug solution C, other disease display unit 69b indicating the occurrence status of other diseases, and a side-effect display unit 69c indicating possible side-effects and their percentages. The information in the cumulative information unit 69a is an analysis result based on personal data, and the information in the side-effect display unit 69c is a prediction result by machine learning.

Figure 19:
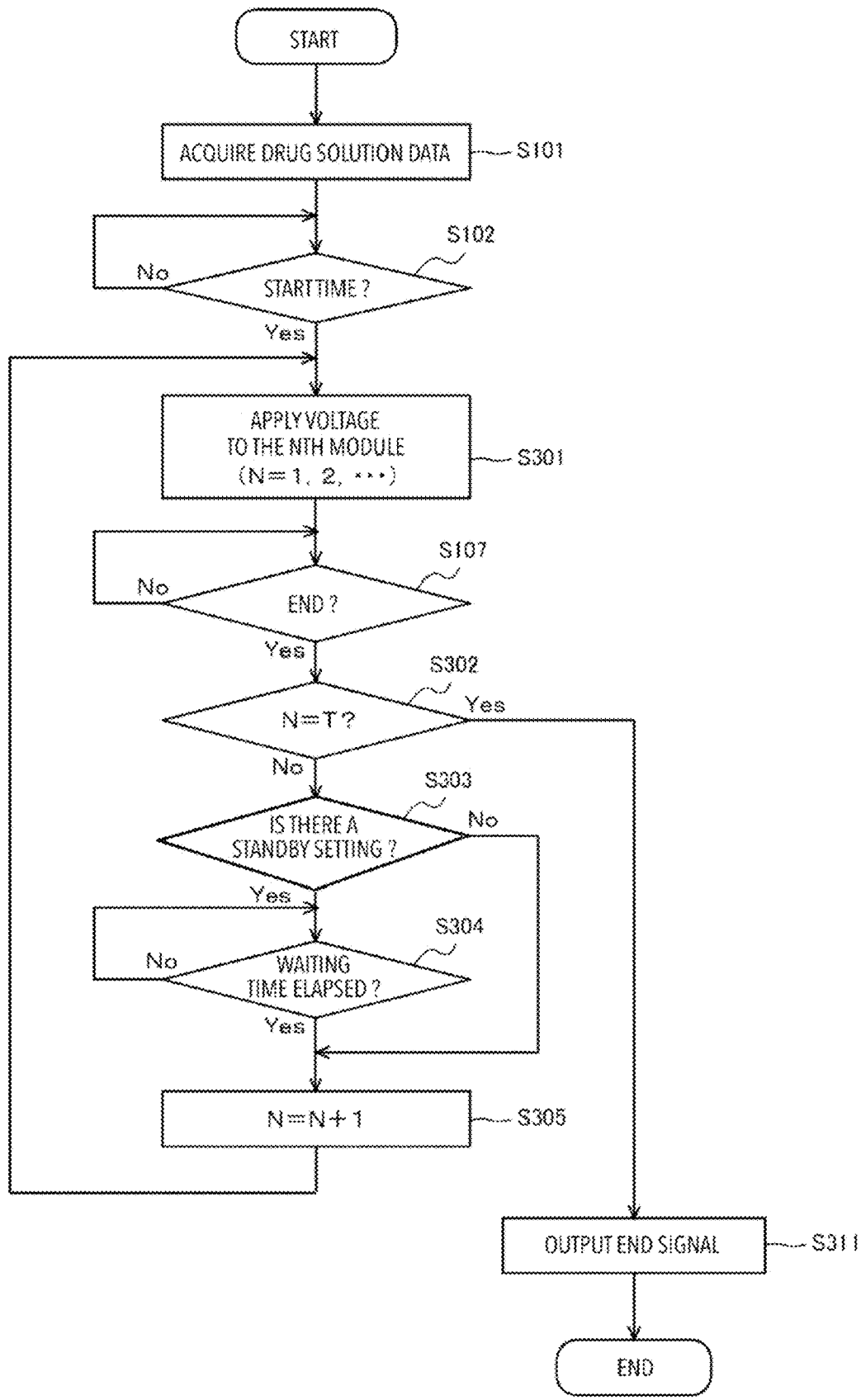
FIG. 19 is a flow chart showing an operation example of the drug solution administration device of FIG. 15.

Next, with reference to the flowchart in FIG. 19, a method for administering a drug solution by the communication processing unit 130 according to the second embodiment will be described. FIG. 19 is a flowchart, based on the setting in which only one drug solution administration module 40 applies a voltage at one time, and indicates an operation related to the combination of both the continuous pattern and the intermittent pattern as described above.

Here, the setting is such that the drug solution C1, the drug solution C2, and the drug solution C3 are sequentially administered, while there is a standby setting between the administration of the drug solution C1 and the administration of the drug solution C2, and there is no standby setting between the administration of the drug solution C2 and the administration of the drug solution C3. The module 40 that is the Nth (N=1, 2, . . . ) controlled object by the control unit 32 is also referred to as the Nth module. The same steps as those in FIG. 10 are designated by the same step numbers and description thereof will be omitted. First, the communication processing unit 130 executes the processes of steps S101 and S102 as in the example of FIG. 10.

Next, the drive processing means 32b applies a voltage of an amount corresponding to the drug solution data to the pair of electrodes (44a, 44b) of the module 40 that is the first control target. Then, in the drive mechanism unit 43, the driving force is transmitted to the drug solution C1 in the second flow path 42b by the movement of the drive solution F caused by the electroosmotic flow, and the drug solution C1 is administered (step S301).

The drive processing means 32b waits until the administration of the drug solution C1 is completed (step S107/No), and when the administration of the drug solution C1 is completed (step S107/Yes), judges whether the control number N is equivalent to the module number T that is the number of module 40 mounted. It is determined whether it is equal to T (step S302). In this assumption, the control number N is 1 and the module number T is 3 (step S302/No), the drive processing means 32b judges whether the waiting time is set between the administration of the first module and the administration of the second module (step S303).

In this assumption, since the waiting time is set (step S303/Yes), the drive processing means 32b waits until the waiting time elapses (step 304/No). When the waiting time has elapsed (step S304/Yes), the drive processing means 32b increments the control number N to 2 (step S305) and applies a voltage to the concerned module at the amount corresponding to the drug solution data of the second module, and the administration of the drug solution C2 is started (step S301).

When the administration of the drug solution C2 is completed (step S107/Yes), here the control number N is 2 and the module number T is 3 (step S302/No), and the waiting time between the administration of the first module and the administration of the second module is not set (step S303/No). Therefore, the drive processing means 32b increments the control number N as 3 (step S305), applies a voltage to the concerned module at the rate corresponding to the drug solution data of the third module and starts the administration of the drug solution C3 (step S301).

When the administration of the drug solution C3 is completed (step S107/Yes), since the control number N is 3 and the module number T is 3 here (step S302/Yes), the drive processing means 32b outputs the end signal to the output processing means 32c. The output processing means 32c causes the output unit 35 to output information indicating the end of administration of the drug solution C in response to the end signal (step S111).

As described above, also by the drug solution administration unit 110 of the second embodiment, according to the applied voltage to the pair of electrodes (44a, 44b) of each drug solution administration module 40, the drug solution C in the second flow path 42b is instantly pushed towards the downstream side, quick and stable administration of the drug solution can be realized without hassles. Further, the medication management system 100 according to the second embodiment can perform fine flow rate adjustment for each module 40 based on a plurality of patterns regarding flow rate setting and control of module 40 (see FIG. 16) and the combination of thereof.

Here if a plurality of syringe pumps are used, it is possible to administer a plurality of drug solutions C in combination, but the operation and management become complicated, lacking practicality. In this regard, the medication management system 100 according to the second embodiment can adjust the flow rates of the plurality of modules 40 by using, for example, the confirmation operation screen shown in FIG. 17, and at least the information indicating the change of the flow rate can be accumulated in the analysis processing device 70. Therefore, it is possible to improve operability and facilitate data management.

By the way, for the treatment of diabetes, insulin with the function of lowering blood sugar has been widely used. However, the administration of insulin is a standardized treatment for diabetic patients, and in fact, there could be such case when the dose of insulin is not appropriate, or when insulin administration itself is not always the most appropriate treatment. Under such circumstances, if formal administration of insulin is continued, it may impede the healing of diabetes or cause a risk of complications.

In this regard, the drug solution administration device 120 according to the second embodiment can be equipped with a plurality of modules 40, and the learning processing means 72b uses each prediction model for obtaining prediction data corresponding to the plurality of modules 40. Therefore, the prediction processing means 72c can predict, for example, not only the necessity of increasing/decreasing insulin, but also the necessity of administration of another hormone or the like having good compatibility with insulin and the flow rate thereof. Therefore, the efficacy of insulin can be enhanced and the healing of the patient is facilitated.

Also, when administering anticancer drug to a patient, a painkiller and a pressor are also administered. Even in such a situation, the analysis processing device 70 can predict the optimal ratio of the anti-cancer drug, the analgesic, and the pressor using a prediction model based on machine learning, so that the balance of the combination of the three can be maintained well, aiming to mitigate side effects. And for each patient, a cancer chemotherapy regimen management, a drug history management, and a mixing adjustment of the drug solution C and the like can be performed quickly and efficiently.

In the above description, the example in which the control unit 32 directly controls the operations of the plurality of drug solution administration modules 40 has been shown, but the present invention is not limited to this. In addition to the communication processing unit 130, the drug solution administration device 120 may include a sub-control unit that is associated with each of the plurality of the drug solution administration modules 40 in a one-on-one correspondence. In this case, for example, the control unit 32 of the communication processing unit 130 may supervise the entire control by co-ordinating with the sub-control unit.

Other effects and the like are similar to those of the first embodiment described above. Further, the alternative configuration and the configurations of the modification examples 1a and 1b described in the first embodiment can also be applied to the drug solution administration unit 110, the drug solution administration device 120, and the medication management system 100, and similar effect can be obtained.

Third Embodiment

Figure 20:
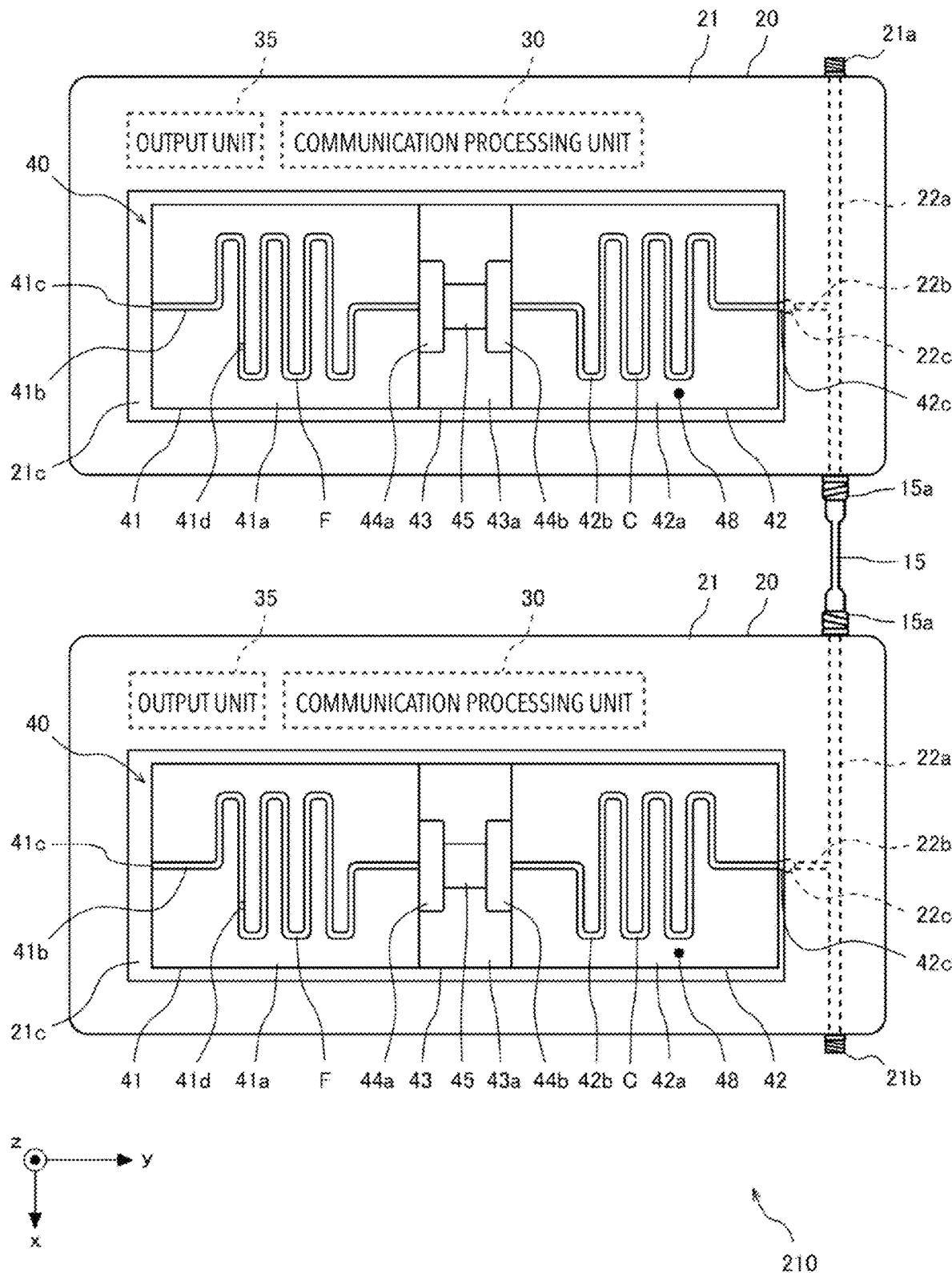
FIG. 20 is a diagram showing one example of the drug solution administration unit according to Embodiment 3 of the present invention.
Figure 21:
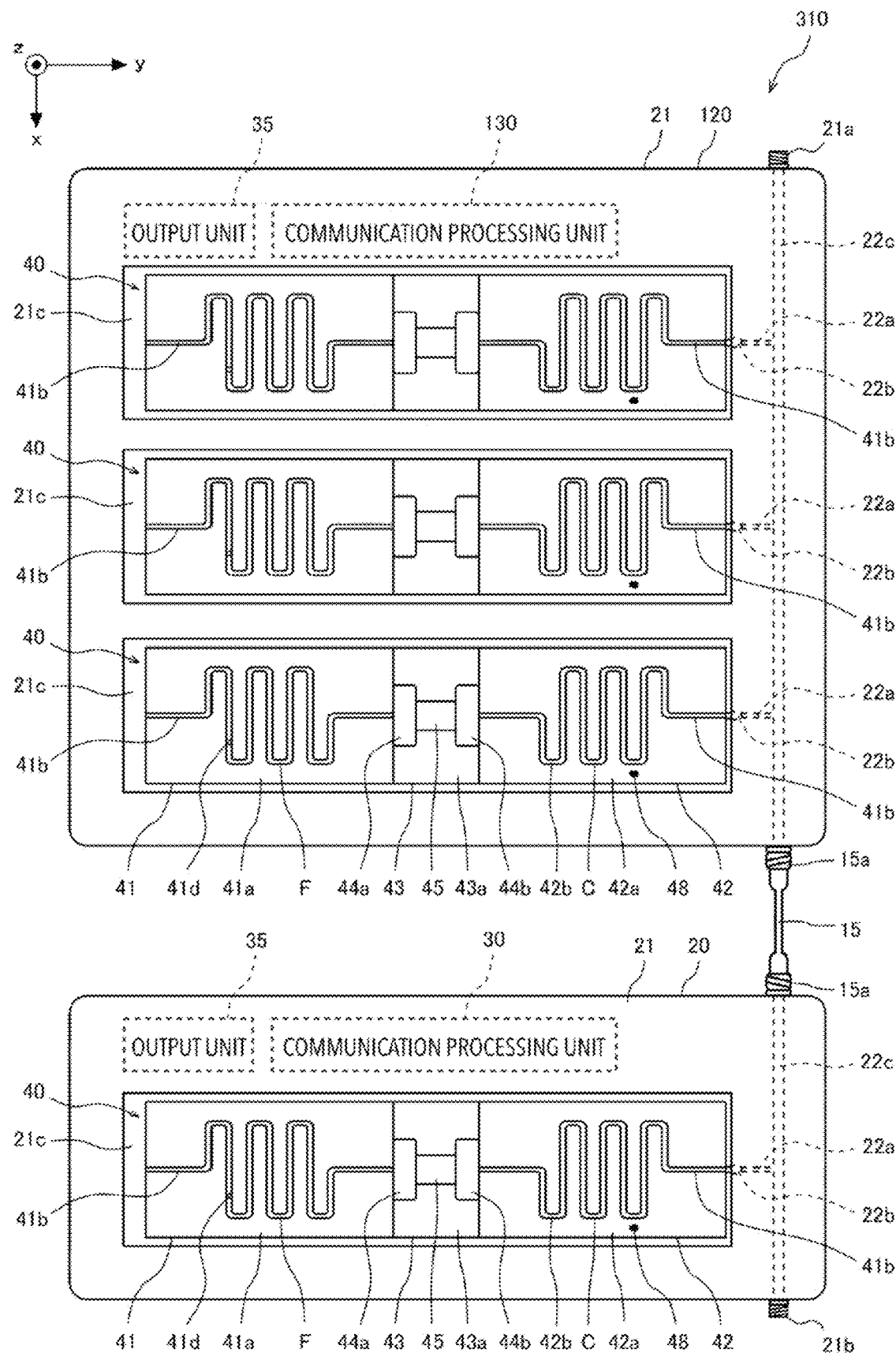
FIG. 21 is a diagram showing the other example of the drug solution administration unit according to Embodiment 3 of the present invention.

The drug solution administration unit according to the third embodiment is characterized in having a plurality of drug solution administration devices and these main paths 22c are connected to each other. That is, the drug solution administration unit is configured by connecting a plurality of drug solution administration device being connected in a daisy chain shape. Further, the control unit 32 of the communication processing unit in each drug solution administration device control the operation of the module 40 that associated itself in co-operation with each other. With reference to FIG. 20 and FIG. 21, the configuration of the drug solution administration unit according to the third embodiment will be described.

FIG. 20 is an example of a drug solution administration unit 210 configured by combining a plurality of drug solution administration devices 20 according to the first embodiment. The drug solution administration device 210 of FIG. 20 is on in which two drug solution administration devices 20 are connected, and a downstream connecting unit 21b of one drug solution administration device 20 and an upstream connecting unit 21a of the other drug solution administration device 20 are connected by a connecting member 15. The connecting member 15 has connectors 15a at both ends. In the drug solution administration unit 210, a main path 22c of the one drug solution administration device 20, the connecting member 15, and the main path 22c of the other drug solution administration device 20 form a continuous flow path.

FIG. 21 is an example of a drug solution administration unit 310 configured by combining the drug solution administration device 20 of the first embodiment and the drug solution administration device 120 of the second embodiment. The drug solution administration unit 310 of FIG. 21 is one in which one drug solution administration device 20 and the drug solution administration device 120 are connected, and the downstream connecting unit 21b of the drug solution administration device 120 and the upstream connecting unit 21a of the drug solution administration unit 20 are connected by the connecting member 15. In the drug solution administration unit 310, the main path 22c of the drug solution administration device 120, the connecting member 15, and the main path 22c of the other drug solution administration device 20 form a continuous flow path.

As described above, also by the drug solution administration module 40, the drug solution administration device 120, and the drug solution administration unit 110 of the third embodiment, according to the voltage application to the pair of electrodes (44a, 44b) of each drug solution administration module 40, because the drug solution C in the second flow path 42b is immediately pushed out towards the downstream side, quick and stable administration of the drug solution can be realized without hassles.

Further, the drug solution administration unit 210 of the third embodiment has a plurality of drug solution administration devices (20, 120). The control units 32 of the plurality of drug solution administration devices (20, 120) co-operate with each other to control the operation of the drive mechanism unit 43 of the module 40 associated with itself. Therefore, similarly to the drug solution administration device 120 capable of mounting the plurality of modules 40, each operation of the plurality of modules 40 can be controlled by the plurality of control patterns as shown in FIG. 16 and the control pattern combining these.

Other effects are similar to the above-described first and second embodiments. In addition, the alternative configurations and the configurations of the modification examples 1a and 1b described in the first and second embodiments are the same as the drug solution administration unit (210, 310), the drug solution administration device (20,120) and the medication management system 100 according to the third embodiment, and the same effect can be obtained.

Fourth Embodiment

Figure 22:
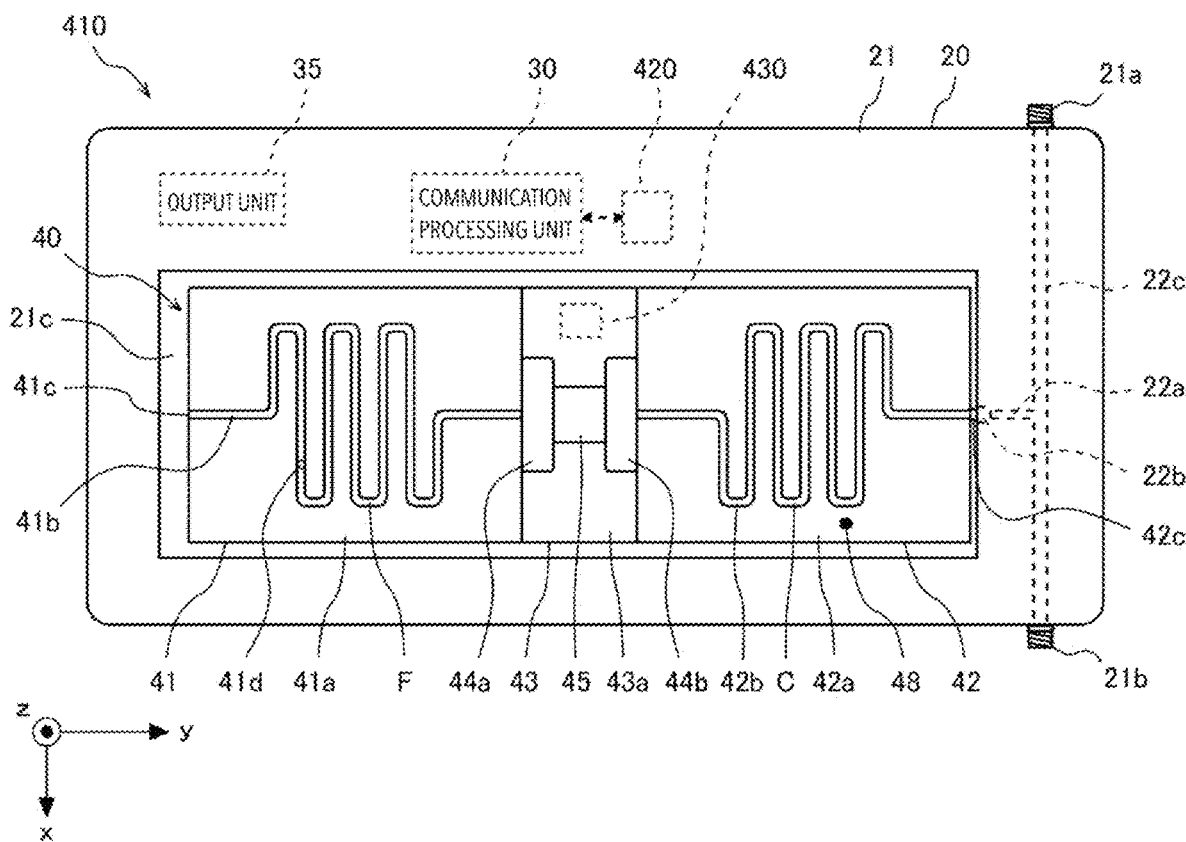
FIG. 22 is a block diagram illustrating the drug solution administration unit according to Embodiment 4 of the present invention.

With reference to FIG. 22, a characteristic configuration of the drug solution administration unit 410 of this fourth embodiment will be described. Constituent members equivalent to those in the first to third embodiments described above are designated by the same reference numerals, and description thereof will be omitted.

The drug solution administration module 40 according to the fourth embodiment is provided with the tag unit 430 having tag information which is unique identification information. The drug solution administration device 20 according to the fourth embodiment is provided with a reading unit 420 that reads tag information from the tag unit 430. The arrangement of the tag unit 430 as well as the arrangement of the reading unit 420 is not limited to the example of FIG. 22. The tag unit 430 is arranged at a position where it can be read by the reading unit 420.

The reading unit 420 and the tag unit 430 can be configured by RFID (Radio Frequency Identification). In this regard, the tag unit 430 is an RF tag (IC Tag) and the reading unit 420 is an RFID reader having a function of reading tag information which is identification information of the tag unit 430. The tag unit 430 is preferably a passive RF tag from the viewpoint of cost. The tag unit 430 may be a one-dimensional code, such as a bar code or a two-dimensional code such as a QR Code (registered trademark: the same applies below) and the like. In this regard, the reading unit 420 is configured to include a camera.

The memory unit 33 stores the related information related to the tag information of the module 40 to be mounted. The related information may be the same information as the tag information. When the module 40 is mounted on the drug solution administration device 20, the reading unit 420 reads the tag information from the tag unit 430 and transmits the read tag information to the control unit 32. The information processing means 32a of the control unit 32 collates the tag information transmitted from the reading unit 420 with the related information to determine whether the mounted module 40 is appropriate, that is, whether the tag information and the related information correspond to each other. The information processing means 32a transmits the result of the determination to the management device 60 via the terminal device 50.

When the nonconformity information, indicating that the implemented module 40 is non-conforming, is transmitted from the control unit 32, the management control unit 62 of the management device 60 causes the display unit 65 to display the information indicating the nonconformity of the module 40, for example. The management control unit 62 may notify a sound or voice from a speaker (not shown) as the information indicating the nonconformity of the module 40.

When the nonconformity information is transmitted from the control unit 32, the terminal control unit 52 of the terminal device 50 may display the information indicating the nonconformity of the module 40 on the terminal display unit 54b, for example. The terminal control unit 52 may, as the information indicating non-conformity of the module 40, notify the sound or voice from the notification unit 55, or operate vibration means (not shown) that causes vibration.

In the above description, an example in which the communication processing unit 30 performs a collation process between the tag information and related information performed by the communication processing unit 30 is described, but the present invention is not limited to this. The collation process between the tag information and related information may be performed by the terminal device 50, the management device 60, or the analysis processing device 70. When such a configuration is adapted, it is preferable to let each device in advance store the device identification information, which is one of the identification information unique to the drug solution administration device 20, and the related information associated with this device identification information. Then, the communication processing unit 30 may transmit the device identification information and the tag information to the terminal device 50 or the like. In addition, the control unit 32 of the communication processing unit 30 may cause the output unit 35 to output information indicating the nonconformity of the module 40 when the mounted module 40 is not suitable.

As described above, the drug solution C in the second flow path 42b is immediately pushed out to the downstream side corresponding to the voltage application to the pair of electrodes (44a, 44b) of each module 40 by the drug administration device 20 and the drug solution administration unit 410 according to the fourth embodiment, and quick and stable administration of the drug solution can be realized without hassles.

Here, a mistaken administration of the drug solution C may cause a great loss to the patient and may lead to a life-threatening situation. In this regard, in the drug solution administration device 20 according to the fourth embodiment of the present invention is provided with the reading unit 420 that reads the tag information from the tag unit 430 that is provided in the module 40 and has the tag information unique to the module 40. Therefore, in the medication management system 100 according to the fourth embodiment, when the module 40 attached to the drug solution administration device 20 differs from the setting, at least one of the communication processing unit 30, the terminal device 50, and the management device 60 outputs the information that indicates the non-conformity of the module 40. Therefore, it is possible to suppress the administration error of the drug solution C and avoid the situation where the incorrect drug solution C is continuously administered for a long time.

The configuration of the fourth embodiment can be applied to the first to third embodiments described above, and the same effect can be obtained. For example, when the configuration of the fourth embodiment is applied to the drug solution administration device 120 that can mount the plurality of modules 40, the identification information of each of the containment units 21c may be good to be used for collation processing.

The above-described embodiments are preferred specific examples of the drug solution administration unit, the drug solution administration module, the drug solution administration device, and the medication management system, and the technical scope of the present invention is not limited to these aspects. For example, FIG. 2 and the like show an example in which the first flow path 41b has three curved paths when one round trip in the bending direction of the bending portion 41W is used as the curved path, but the present invention is not limited to this. The first flow path 41b may have two and a half curved paths or less, and may have three and a half curved paths or more. Similarly, FIG. 2 shows an example in which the second flow path 42b has three curved paths when one round trip in the bending direction of the bending portion 42W is set as the curved path, but the present invention is not limited to this. The second flow path 42b may have two and a half curved paths or less, and may have three and a half or more curved paths.

In FIG. 2 and the like as the shapes of the bending portion 41W and the bending portion 42W, a meandering shape that meanders in the bending direction is illustrated, but the shape is not limited to this. As the shape of the bending portion 41W or the bending portion 42W, various shapes can be adopted such as an S-shape, a continuous S-shape, or a combination of these with a meandering shape and the like. Of course the bending portion 41W and the bending portion 42W may adopt a three-dimensional shape such as a multi-stage flow path configuration, a spiral flow path configuration or the like, but in consideration of the difficulty of processing, a single-stage flow path configuration is preferred. The first flow path 41b and the second flow path 42b are, by being formed thin, that is, by shortening the length towards the bending direction or the thickness direction, able to suppress convection. Therefore, when the solution amount can be secured, the first flow path 41b and the second flow path 42b may be formed thin and the bending portion may be simplified to have, for example, an arched shape.

The position of the remaining amount sensor 48 is not limited to the position shown in each figure, and can be arbitrarily arranged. For example, the remaining amount sensor 48 may be provided in the first flow path unit 41. Further, a plurality of remaining amount sensors 48 may be provided in one module 40. In each of the above drawings, the upstream side main body 41a, the drive unit main body 43a, and the downstream side main body 42a are integrated, but the present invention is not limited to this, and the upstream side main body 41a, the drive unit main body 43a, and the downstream side main body 42a may be separated from each other. It should be noted that the learning processing means 73b may construct one prediction model for obtaining both the recommended flow rate and the vital prediction information.

The medication management system 100 may be configured by at least one out of the drug solution administration device (20, 120), the terminal device 50, the management device 60, and the analysis processing device 70. That is, for example, the medication management system 100 may be configured by the drug solution administration device (20, 120) and the terminal device 50; or may be configured by the drug solution administration device (20, 120) and the management device 60; or may be configured by the drug solution administration device (20, 120), the management device 60 and the analysis processing device 70.

The prediction processing means 72c may have a feed-forward function of generating prediction data by reflecting future actions. And, the prediction processing means 72c may store table information in which some parameters are associated with the flow rate of the drug solution C and the like in the analysis memory unit 73 when the data used for generating the prediction data is less. And, the prediction processing means 72c may obtain the recommended flow rate value by comparing the setting data with the table information.

REFERENCE SIGNS LIST

| | |
|---|---|
| 10, 110, 210, 310, 410 | drug solution administration unit |
| 15 | connecting member |
| 15a | connector |
| 20, 120 | drug solution administration device |
| 21 | housing |
| 21a | upstream connecting unit |
| 21b | downstream connecting unit |
| 21c | containment unit |
| 22a | branch path |
| 22b | flow path connecting unit |
| 22c | main path |
| 30, 130 | communication processing unit |
| 31 | communication unit |
| 32 | control unit |
| 32a | information processing means |
| 32b | drive processing means |
| 32c | output processing means |
| 33 | memory unit |
| 33p | drug solution administration program |
| 35 | output unit |
| 35a | light emitting means |
| 35b | notification means |
| 40 | drug solution administration module (module) |
| 41 | first flow path unit |
| 41W, 42W | bending portion |
| 41a | upstream side main body |
| 41b | first flow path |
| 41c | vent hole |
| 41d | following member |
| 42 | second flow path unit |
| 42W | bending portion |
| 42a | downstream side main body |
| 42b | second flow path |
| 42c | drug solution connecting unit |
| 43 | drive mechanism unit |
| 43a | drive unit main body |
| 44a, 44b | electrodes |
| 45 | porous body |
| 48 | remaining amount sensor |
| 50 | terminal device |
| 51 | terminal communication unit |
| 52 | terminal control unit |
| 52a | communication processing means |
| 52b | display processing means |
| 53 | terminal memory unit |

-continued

| | |
|---|---|
| 54 | input display unit |
| 54a | terminal input unit |
| 54b | terminal display unit |
| 55 | notification unit |
| 56 | safety switch |
| 56x | cursor |
| 57 | slide bar |
| 57x | cursor |
| 57y | flow rate display unit |
| 57z | status display unit |
| 58 | instruction button |
| 59 | return button |
| 60 | management device |
| 61 | management communication unit |
| 62 | management control unit |
| 62a | information processing means |
| 62b | display processing means |
| 63 | management memory unit |
| 64 | input unit |
| 65 | display unit |
| 66a | patient's selection column |
| 66b | attribute display column |
| 66c | flow rate display column |
| 67 | prediction column |
| 67a | recommended information |
| 67b | prediction unit |
| 67c | post-change prediction unit |
| 68x | effect information |
| 68y | side-effect information |
| 69 | status display column |
| 69a | cumulative information unit |
| 69b | other disease display unit |
| 69c | side-effect display unit |
| 70 | analysis processing device |
| 71 | analysis communication unit |
| 72 | analysis control unit |
| 72a | collection processing means |
| 72b | learning processing means |
| 72c | prediction processing means |
| 73 | analysis memory unit |
| 73b | learning processing means |
| 73p | analysis processing program |
| 80 | intravenous unit |
| 81 | infusion container |
| 82 | intravenous tube |
| 83 | klemme |
| 85 | tube |
| 85a | upstream side connector |
| 85b | downstream side connector |
| 90 | stand |
| 91 | leg portion |
| 92 | column |
| 93 | bottle hook |
| 94 | handle portion |
| 100 | medication management system |
| 166c | flow rate display column |
| 420 | reading unit |
| 430 | tag unit |
| 680 | countermeasure key |
| 731 | flow rate prediction model |
| 732 | vital prediction model |
| C, C1-C3 | drug solution |
| F | drive solution |
| N | control number |
| Ne | network |
| T | number of modules |
| W | waiting time |
| Y | infusion |

What is claimed is:

1. A drug solution administering unit, comprising:
a drug solution administration module comprising
a first flow path unit including an upstream side main body where a first flow path to store drive solution is formed,
a second flow path unit including a downstream side main body where a second flow path to store drug solution is formed, and
a drive mechanism unit including a pair of electrodes and a porous body sandwiched between the pair of electrodes, the drive mechanism unit having a connecting flow path connecting a downstream end of the first flow path and an upstream end of the second flow path; and
a drug solution administration device to which the drug solution administration module is mounted,
wherein the drug solution administration module has a drug solution connecting unit at a downstream end of the second flow path,
the drug solution administration device comprising:
a housing where a containment unit to store the drug solution administration module is formed,
inside of the housing, a branch path where the second flow path is connected, and
inside of the housing, a main path that is branched from a downstream side of the branch path and connected to an intravenous tube,
the main path connects an upstream connecting unit with a downstream connecting unit,
the upstream connecting unit connects the main path with the intravenous tube on an upstream side,
the downstream connecting unit connects the main path with the intravenous tube on a downstream side,
wherein the drug solution administration device has a flow path connecting unit at an upstream end of the branch path to which the drug solution connecting unit is connected.

2. The drug solution administration unit as claimed in claim 1, wherein
the drug solution administration device further comprising a control unit being connected to the pair of electrodes for controlling an operation of the drive mechanism unit.

3. The drug solution administration unit as claimed in claim 2, wherein
the housing has a plurality of the containment units to store a plurality of the drug solution administration modules.

4. The drug solution administration unit as claimed in claim 3, comprising the plurality of the drug solution administration modules,
wherein the control unit controls operation of a respective drive mechanism unit of each drug solution administration module based on flow rate data indicating flow rate of drug solution administration by the plurality of the drug solution administration modules and administration data indicating a timing of the drug solution administration.

5. The drug solution administration unit as claimed in claim 1,
wherein the intravenous tube is configured to receive an infusion solution; and
wherein the drug solution administration module is configured to dispense the drug solution via the drug solution connecting unit and mix the drug solution with the infusion solution in the main path.

* * * * *